US007741461B2

(12) United States Patent
Smith et al.

(10) Patent No.: US 7,741,461 B2
(45) Date of Patent: *Jun. 22, 2010

(54) NUCLEIC ACID PROBES AND METHODS FOR DETECTING CLINICALLY IMPORTANT FUNGAL PATHOGENS

(75) Inventors: Terry Smith, Galway (IE); Majella Maher, Galway (IE); Cara Martin, Louth (IE); Geert Jannes, Leuven (BE); Rudi Rossau, Ekeren (BE); Marjo Van der Weide, Terneuzen (NL)

(73) Assignees: Innogenetics N.V., Ghent (BE); Enterprise Ireland, Dublin (IE); National University of Ireland Galway, Galway (IE)

( * ) Notice: Subject to any disclaimer, the term of this patent is extended or adjusted under 35 U.S.C. 154(b) by 970 days.

This patent is subject to a terminal disclaimer.

(21) Appl. No.: 10/967,254

(22) Filed: Oct. 19, 2004

(65) Prior Publication Data

US 2005/0164243 A1 Jul. 28, 2005

Related U.S. Application Data

(62) Division of application No. 09/662,462, filed as application No. PCT/EP00/04714 on May 24, 2000, now Pat. No. 6,858,387.

(60) Provisional application No. 60/138,621, filed on Jun. 11, 1999.

(30) Foreign Application Priority Data

May 28, 1999 (EP) .................................. 99870109

(51) Int. Cl.
*C07H 21/04* (2006.01)
*C12Q 1/68* (2006.01)

(52) U.S. Cl. ..................... 536/23.1; 536/24.3; 435/6; 435/91.1; 435/91.2

(58) Field of Classification Search ....................... None
See application file for complete search history.

(56) References Cited

U.S. PATENT DOCUMENTS

| | | |
|---|---|---|
| 4,617,102 A | 10/1986 | Tomblin |
| 5,426,027 A | 6/1995 | Lott et al. |
| 5,558,989 A | 9/1996 | Shah |
| 5,595,874 A | 1/1997 | Hogan |
| 5,631,132 A | 5/1997 | Lott et al. |
| 5,693,501 A | 12/1997 | Lee et al. |
| 5,814,453 A | 9/1998 | Beck |
| 5,827,695 A | 10/1998 | Beck |
| 5,874,221 A | 2/1999 | Tooley et al. |
| 5,955,274 A | 9/1999 | Ligon et al. |
| 6,017,699 A | 1/2000 | Jordan |
| 6,071,698 A | 6/2000 | Beck |
| 6,080,543 A | 6/2000 | Engel et al. |
| 6,242,178 B1 | 6/2001 | Lott |
| 6,858,387 B1 * | 2/2005 | Smith et al. .................... 435/6 |

FOREIGN PATENT DOCUMENTS

| | | |
|---|---|---|
| EP | 0 642 588 A1 | 11/1993 |
| EP | 0 894 870 A2 | 2/1999 |
| WO | WO 93/23568 | 11/1993 |
| WO | WO 95 29260 A | 11/1995 |
| WO | WO 96 21741 A | 7/1996 |
| WO | WO 97/36003 | 10/1997 |
| WO | WO 98 11257 A | 3/1998 |
| WO | WO 98 50584 A | 11/1998 |
| WO | WO 99 06596 A | 2/1999 |

OTHER PUBLICATIONS

Lin (Genbank Accession No. U10987, Mar. 1996).
Lin et al., J. of Clinical Microbiology, vol. 33, No. 7, pp. 1815-1821, Jul. 1995.
Messner et al, Genbank Acceession No. U09325, May 1994.
Williams et al, Genbank Accession No. L47108, Sep. 1995.
EMBL Accession No. U96719, Lott, Aug. 1997.
Williams et al, J. Clin Pathol., vol. 49, pp. M23-M28, 1996.
Fujita et al, "Microtitratin Plate Enzyme Immunoassay to Detect . . . ", Journal of Clinical Microbiology, U.S., Washington, D.C., vol. 33, No. 4, Apr. 1, 1995, pp. 962-967, XPOO2053345.
Elie et al, "Rapid identification of Candida species with species-specific DNA probes", Journal of Clinical Microbiology, U.S., Washington, D.C., vol. 36, No. 11, Nov. 1, 1998, pp. 3260-3265; XP002086007.
Shin et al, "Rapid identification of up to three Candida species in a single . . . ", Journal of Clinical Microbiology, vol. 37, No. 1, 1999, pp. 165-170, XP00874684.
Botelho and Planta, "Specific Identification of Candida albicans by hybridization . . . ", Yeast, vol. 10, 1994, pp. 709-717, XP000874680.
White et al, "Amplification and Direct Sequencing of Fungal Ribosomal . . . ", U.S. San Diego, Academic Press, 1989, pp. 315-322, XP002017490.
Database Genback [Online] Accession No. (AC): Y14001, 1997 Zakikhani S and Kappe R: "Internal transcribed spaces (ITS1) of the ribosomal cluster of Candida albicans", XP002130403.
Nho et al, "Species differentiation by internally transcribed spacer PCR . . . ", Journal of Clinical Microbiology, U.S., Washington, D.C., vol. 35, No. 4, Apr. 1, 1997 pp. 1036-1039, XP002086004.

(Continued)

*Primary Examiner*—Jeanine A Goldberg
(74) *Attorney, Agent, or Firm*—Nixon & Vanderhye P.C.

(57) ABSTRACT

The current invention relates to the field of detection and identification of clinically important fungi. More particularly, the present invention relates to species specific probes originating from the Internal Transcribed Spacer (ITS) region of rDNA for the detection of fungal species such as *Candida albicans, Candida parapsilosis, Candida tropicalis, Candida kefyr, Candida krusei, Candida glabrata, Candida dubliniensis, Aspergillus flavus, Aspergillus versicolor, Aspergillus nidulans, Aspergillus fumigatus, Cryptococcus neoformans* and *Pneumocystis carinii* in clinical samples, and methods using said probes.

9 Claims, 2 Drawing Sheets

OTHER PUBLICATIONS

Figure 1:
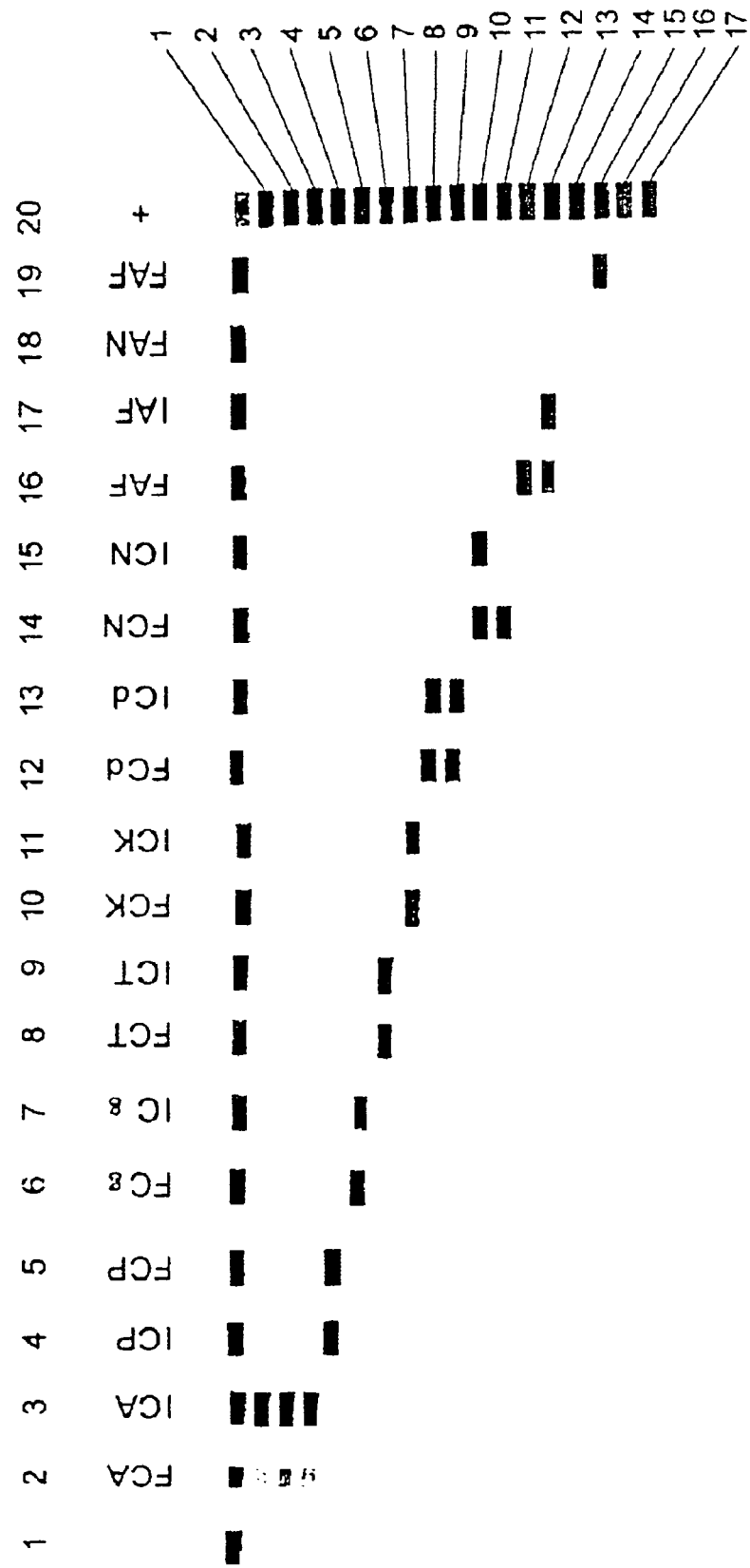

Database Genback [Online] Accession No. (AC): Y14002, 1997 Zakikhani S and Kappe R: "Internal transcribed spacers (ITS1) of the ribosomal cluster of Candida albicans", XP002153730.

Loffler et al, "Comparison of different methods for extraction of DNA of fungal pathogens . . .", Journal of Clinical Microbiology, vol. 35, No. 12, 1997, pp. 3311-3312, XP000961790.

Jordan, "PCR identification of four medically important Candida . . . ", Journal of Clinical Microbiology, vol. 32, No. 12, 1994, pp. 2962-2967, XP000961788.

Irobi et al, "Mol. Cell. Probes", 1999; 14:401-406.

Lu et al, 1995; 33:2973-2977.
Einsele et al, JCM, 1997; 35:1353-1360.
Sugita et al, JCM, 1999; 37:1985-1993.
Makimura et al, JCM, 1999, 37:920-924.
Jackson et al, JCM, 1999; 37:931-936.
Turenne et al, JCM, 1999; 37:1846-1851.
Jiang et al, JCM, 2000; 38:241-245.
Henry et al, JCM, 2000; 38:1510-1515.
Gupta et al, JCM, 2000; 38:1869-1875.
Tintelnot et al, JCM, 2000; 38:1599-1608.
Posteraro et al, JCM, 2000; 38:1609-1614.

* cited by examiner

```
                            SEQUENCE LISTING

<160> NUMBER OF SEQ ID NOS: 43

<210> SEQ ID NO 1
<211> LENGTH: 20
<212> TYPE: DNA
<213> ORGANISM: Candida albicans

<400> SEQUENCE: 1
gtctaaactt acaaccaatt                                               20

<210> SEQ ID NO 2
<211> LENGTH: 20
<212> TYPE: DNA
<213> ORGANISM: Candida albicans

<400> SEQUENCE: 2
tgtcacacca gattattact                                               20

<210> SEQ ID NO 3
<211> LENGTH: 20
<212> TYPE: DNA
<213> ORGANISM: Candida albicans

<400> SEQUENCE: 3
tatcaacttg tcacaccaga                                               20

<210> SEQ ID NO 4
<211> LENGTH: 18
<212> TYPE: DNA
<213> ORGANISM: Candida parapsilosis

<400> SEQUENCE: 4
gtaggccttc tatatggg                                                 18

<210> SEQ ID NO 5
<211> LENGTH: 20
<212> TYPE: DNA
<213> ORGANISM: Candida parapsilosis

<400> SEQUENCE: 5
tgccagagat taaactcaac                                               20

<210> SEQ ID NO 6
<211> LENGTH: 20
<212> TYPE: DNA
<213> ORGANISM: Candida tropicalis

<400> SEQUENCE: 6
ggttataact aaaccaaact                                               20
```

<210> SEQ ID NO 7
<211> LENGTH: 20
<212> TYPE: DNA
<213> ORGANISM: Candida kefyr

<400> SEQUENCE: 7
ttttccctat gaactacttc                                               20

<210> SEQ ID NO 8
<211> LENGTH: 18
<212> TYPE: DNA
<213> ORGANISM: Candida kefyr

<400> SEQUENCE: 8
agagctcgtc tctccagt                                                 18

<210> SEQ ID NO 9
<211> LENGTH: 20
<212> TYPE: DNA
<213> ORGANISM: Candida krusei

<400> SEQUENCE: 9
ggaatatagc atatagtcga                                               20

<210> SEQ ID NO 10
<211> LENGTH: 19
<212> TYPE: DNA
<213> ORGANISM: Candida glabrata

<400> SEQUENCE: 10
gagctcggag agagacatc                                                19

<210> SEQ ID NO 11
<211> LENGTH: 20
<212> TYPE: DNA
<213> ORGANISM: Candida dubliniensis

<400> SEQUENCE: 11
tagtggtata aggcggagat                                               20

<210> SEQ ID NO 12
<211> LENGTH: 17
<212> TYPE: DNA
<213> ORGANISM: Candida dubliniensis

<400> SEQUENCE: 12
ctaaggcggt ctctggc                                                  17

<210> SEQ ID NO 13
<211> LENGTH: 20
<212> TYPE: DNA
<213> ORGANISM: Candida dubliniensis

<400> SEQUENCE: 13
gttttgttct ggacaaactt                                               20

<210> SEQ ID NO 14
<211> LENGTH: 20
<212> TYPE: DNA
<213> ORGANISM: Cryptococcus neoformans

<400> SEQUENCE: 14

-continued

```
cttctaaatg taatgaatgt                                         20

<210> SEQ ID NO 15
<211> LENGTH: 20
<212> TYPE: DNA
<213> ORGANISM: Cryptococcus neoformans

<400> SEQUENCE: 15
catctacacc tgtgaactgt                                         20

<210> SEQ ID NO 16
<211> LENGTH: 19
<212> TYPE: DNA
<213> ORGANISM: Cryptococcus neoformans

<400> SEQUENCE: 16
ggacagtaga gaatattgg                                          19

<210> SEQ ID NO 17
<211> LENGTH: 18
<212> TYPE: DNA
<213> ORGANISM: Cryptococcus neoformans

<400> SEQUENCE: 17
ggacttggat ttgggtgt                                           18

<210> SEQ ID NO 18
<211> LENGTH: 21
<212> TYPE: DNA
<213> ORGANISM: Aspergillus flavus

<400> SEQUENCE: 18
gtttactgta ccttagttgc t                                       21

<210> SEQ ID NO 19
<211> LENGTH: 15
<212> TYPE: DNA
<213> ORGANISM: Aspergillus flavus

<400> SEQUENCE: 19
ccgccattca tggcc                                              15

<210> SEQ ID NO 20
<211> LENGTH: 15
<212> TYPE: DNA
<213> ORGANISM: Aspergillus flavus

<400> SEQUENCE: 20
cgggggctct cagcc                                              15

<210> SEQ ID NO 21
<211> LENGTH: 17
<212> TYPE: DNA
<213> ORGANISM: Aspergillus versicolor

<400> SEQUENCE: 21
cctctcgggg gcgagcc                                            17

<210> SEQ ID NO 22
<211> LENGTH: 17
<212> TYPE: DNA
<213> ORGANISM: Aspergillus nidulans

<400> SEQUENCE: 22
```

-continued

```
ccgagtgcgg ctgcctc                                                      17

<210> SEQ ID NO 23
<211> LENGTH: 15
<212> TYPE: DNA
<213> ORGANISM: Aspergillus nidulans

<400> SEQUENCE: 23
ccgagtgcgg gctgc                                                        15

<210> SEQ ID NO 24
<211> LENGTH: 20
<212> TYPE: DNA
<213> ORGANISM: Aspergillus nidulans

<400> SEQUENCE: 24
gagcctgaat accaaatcag                                                   20

<210> SEQ ID NO 25
<211> LENGTH: 19
<212> TYPE: DNA
<213> ORGANISM: Aspergillus nidulans

<400> SEQUENCE: 25
gagcctgaat acaaatcag                                                    19

<210> SEQ ID NO 26
<211> LENGTH: 19
<212> TYPE: DNA
<213> ORGANISM: Aspergillus fumigatus

<400> SEQUENCE: 26
gttgattatc gtaatcagt                                                    19

<210> SEQ ID NO 27
<211> LENGTH: 18
<212> TYPE: DNA
<213> ORGANISM: Aspergillus fumigatus

<400> SEQUENCE: 27
gcgacaccca actttatt                                                     18

<210> SEQ ID NO 28
<211> LENGTH: 22
<212> TYPE: DNA
<213> ORGANISM: Pneumocystis carinii

<400> SEQUENCE: 28
atgctagtct gaaattcaaa ag                                                22

<210> SEQ ID NO 29
<211> LENGTH: 21
<212> TYPE: DNA
<213> ORGANISM: Pneumocystis carinii

<400> SEQUENCE: 29
ggattgggct ttgcaaatat t                                                 21

<210> SEQ ID NO 30
<211> LENGTH: 17
<212> TYPE: DNA
<213> ORGANISM: Pneumocystis carinii
```

```
<400> SEQUENCE: 30
ttcgctggga aagaagg                                              17

<210> SEQ ID NO 31
<211> LENGTH: 19
<212> TYPE: DNA
<213> ORGANISM: Pneumocystis carinii

<400> SEQUENCE: 31
gcttgcctcg ccaaaggtg                                            19

<210> SEQ ID NO 32
<211> LENGTH: 25
<212> TYPE: DNA
<213> ORGANISM: Pneumocystis carinii

<400> SEQUENCE: 32
taaattgaat ttcagtttta gaatt                                     25

<210> SEQ ID NO 33
<211> LENGTH: 22
<212> TYPE: DNA
<213> ORGANISM: Candida albicans

<400> SEQUENCE: 33
ttgtcacacc agattattac tt                                        22

<210> SEQ ID NO 34
<211> LENGTH: 24
<212> TYPE: DNA
<213> ORGANISM: Candida albicans

<400> SEQUENCE: 34
ggtttatcaa cttgtcacac caga                                      24

<210> SEQ ID NO 35
<211> LENGTH: 24
<212> TYPE: DNA
<213> ORGANISM: Candida albicans

<400> SEQUENCE: 35
ggtatcaact tgtcacacca gatt                                      24

<210> SEQ ID NO 36
<211> LENGTH: 24
<212> TYPE: DNA
<213> ORGANISM: Candida tropicalis

<400> SEQUENCE: 36
ggttataact aaaccaaact tttt                                      24

<210> SEQ ID NO 37
<211> LENGTH: 21
<212> TYPE: DNA
<213> ORGANISM: Candida krusei

<400> SEQUENCE: 37
gggaatatag catatagtcg a                                         21

<210> SEQ ID NO 38
<211> LENGTH: 21
<212> TYPE: DNA
<213> ORGANISM: Candida dubliniensis
```

```
<400> SEQUENCE: 38
ggttttgttc tggacaaact t                                               21

<210> SEQ ID NO 39
<211> LENGTH: 22
<212> TYPE: DNA
<213> ORGANISM: Cryptococcus neoformans

<400> SEQUENCE: 39
catctacacc tgtgaactgt tt                                              22

<210> SEQ ID NO 40
<211> LENGTH: 21
<212> TYPE: DNA
<213> ORGANISM: Aspergillus fumigatus

<400> SEQUENCE: 40
ccgacaccca actttatttt t                                               21

<210> SEQ ID NO 41
<211> LENGTH: 20
<212> TYPE: DNA
<213> ORGANISM: Aspergillus fumigatus

<400> SEQUENCE: 41
gttgattatc gtaatcagtt                                                 20

<210> SEQ ID NO 42
<211> LENGTH: 19
<212> TYPE: DNA
<213> ORGANISM: Aspergillus flavus

<400> SEQUENCE: 42
gaactctgtc tgatctagt                                                  19

<210> SEQ ID NO 43
<211> LENGTH: 21
<212> TYPE: DNA
<213> ORGANISM: Aspergillus versicolor

<400> SEQUENCE: 43
gtctgaatat aaaatcagtc a                                               21
```

NUCLEIC ACID PROBES AND METHODS FOR DETECTING CLINICALLY IMPORTANT FUNGAL PATHOGENS

This application is a divisional of application Ser. No. 09/662,462, filed Sep. 15, 2000 (allowed) now U.S. Pat. No. 6,858,387, which is a continuation of PCT/EP00/04714, filed 24 May 2000, which designated the U.S., and claims the benefit of U.S. Provisional Application No. 60/138,621, filed 11 Jun. 1999, and EP 99870109.8, filed 28 May 1999, the entire contents of each of which being incorporated herein by reference.

FIELD OF THE INVENTION

The current invention relates to the field of detection and identification of clinically important fungi. More particularly, the present invention relates to species specific probes originating from the Internal Transcribed Spacer (ITS) region of rDNA for the detection of fungal species such as *Candida albicans*, *Candida parapsilosis*, *Candida tropicalis*, *Candida kefyr*, *Candida krusei*, *Candida glabrata*, *Candida dubliniensis*, *Aspergillus flavus*, *Aspergillus versicolor*, *Aspergillus nidulans*, *Aspergillus fumigatus*, *Cryptococcus neoformans* and *Pneumocystis carinii* in clinical samples, and methods using said probes.

BACKGROUND OF THE INVENTION

Fungal infections are becoming an increasingly significant cause of morbidity and mortality. In the course of the 1980s, the rate of bloodstream infection by *Candida albicans* surged by 48%. Patients at particular risk of mycoses are those with diminished immune defenses—not only organ transplant patients or those receiving intensive treatment for cancer, but also diabetics or people with indwelling catheters.

Fungal infections account for a large number of AIDS-defining diagnoses and complicate the course of most patients with HIV disease. The ECHO estimates that there will be more than 20 million HIV-infected adults alive in the year 2000. The impact of fungi disease in AIDS patients is immense because of their recurring nature. Of the 25 conditions which make up the case definition for AIDS, seven are caused by fungal pathogens. Of the most frequent AIDS indicator diseases occurring among homosexual/bisexual men, 70% were fungal infections, with *Pneumocystis carinii* pneumonia (PCP) being the most common of all diseases.

Fungi occur in a wide variety of forms, from yeasts (single-celled organisms which reproduce by budding) and moulds (which occur in long filaments known as hyphae) to the dimorphic fungi which have a chameleon-like ability to behave as yeasts in one environment and mould in another.

Of the many different types of fungi only a few have the potential to cause disease, and the severity of their effects varies widely. Superficial mycoses, caused by a fungus such as *Epidermophyton, Microsporum, Trichophyton* or *Sporothrix* growing on the body surface (skin, nails or hair) are unpleasant but usually mild infections.

Deep mycoses, involving the internal organs, are often life-threatening. The fungi *Aspergillus, Blastomyces, Candida, Coccidioides, Cryptococcus, Histoplasma* are responsible for deep mycoses, and pose tremendous challenges for clinicians. Clinically, candidiasis and aspergillosis account for between 80% and 90% of systemic fungal infections in immunocompromised patients. Recently, infections caused by *Pneumocystis carinii* are more frequently found in AIDS patients.

*Pneumocystis carinii* is a major opportunistic infectious agent in immunocompromised patients, causing pneumonia which has a high mortality rate if the patient is not properly treated (Stringer J. R., 1996). Therefore, timely diagnosis of *P. carinii* pneumonia (PCP) is critical for patient management. Currently, diagnosis of PCP is usually made by morphological demonstration of organisms in bronchoalveolar lavage (BAL) fluid, induced sputum, or specimens obtained by open lung biopsy (Cregan et al., 1990). Although morphological diagnosis is rapid, it requires highly experienced personnel and good specimens. Given the inability to culture *P. carinii* in vitro, molecular biology-based methods have been used for the detection of this pathogen and to study *P. carinii* epidemiology (Lu et al., 1995).

Candidoses comprise a range of human opportunistic infections which may occur in either acute or chronic forms. *Candida* infections frequently arise on the mucosal surfaces of the mouth or vagina. Chronic hyperplastic candidosis of the oral mucosa is of particular importance since it has been associated with the development of squamous cell carcinoma. In addition to superficial lesions, deeper *candida* infections, such as esophagitis and endocarditis, may occur, particularly in immunocompromised individuals (Heimdahl et al., 1990).

In the past, many studies of candidosis have not identified candidal isolates to species level. Indeed, in the case of chronic hyperplastic candidosis, reporting is usually limited to the presence of structures consistent with candidal hyphae following histological examination of lesional tissue. However, it is becoming increasingly recognized that both species and subspecies of *Candida* differ in their ability to cause disease. Traditional methods used for the identification and typing of clinical isolates of *Candida* include morphological and biochemical analysis (Williamson et al., 1986), colony morphotyping (Soll, D. R. 1992), resistogram typing (Sobczak, H., 1985), and serotyping (Brawner, D. L., 1991). These techniques are time-consuming, and their reliance on phenotypic expression makes them potentially unreliable. An alternative method would be one based on genotypic properties. Genotypic methods have been used for the detection and typing of *Candida* strains (Bart-Delabesse et al., 1993; Holmes et al., 1994), but have been used less frequently for differentiation of species.

Other medically important *Candida* species, next to the most frequently isolated pathogen *C. albicans*, are *C. glabrata. C. krusei* and *C. tropicalis*. The latter species are much less susceptible to classical antifungal drugs.

The genus *Cryptococcus* contains many species, wherein *Cryptococcus neoformans* is considered the only human pathogen. Initial cryptococcal infection begins by inhalation of the fungus into the lungs, usually followed by hematogeneous spread to the brain and meninges. Involvement of the skin, bores, and joints is seen, and *Cryptococcus neoformans* is often cultured from the urine of patients with disseminated infection. In patients without HIV infection, cryptococcosis, particularly cryptococcal meningitis, usually is seen in association with underlying conditions such as lupus erythematosis, sarcoidosis, leukemia, lymphomas, and Cushing's syndrome (Chuck et al., 1989).

Cryptococcosis is one of the defining diseases associated with AIDS. Patients with cryptococcosis and serologic evidence of HIV infections are considered to have AIDS. In nearly 45% of AIDS patients, cryptococcosis was reported as the first AIDS-defining illness. Because none of the representing signs or symptoms of cryptococcal meningitis (such as headache, fever, and malaise) are sufficiently characteristic to distinguish it from other infections that occur in patients with AIDS, determining cryptococcal antigen titers and culturing blood and cerebrospinal fluid are useful in making a diagnosis (Chuck et al. 1989).

The clinical diagnosis of pulmonary cryptococcosis in patients without underlying diseases is generally difficult. Since the diagnosis is often established only by examination of tissue obtained from lung biopsy specimens, other more sensitive and specific methods are needed for the simple and fast detection of the fungus. One such approach involves the detection of fungal antigens in serum (Kohno et al., 1993). However, evaluations of serological assays for detecting cryptococcal antigen showed false-positive reactions with sera from patients infected with *Trichosporon beigelii* (Kohno et al., 1993).

Aspergillosis is now considered the second most common fungal infection requiring hospitalization. In patients with positive fungus cultures, *Aspergillus* species are the second most common isolate after *Candida* species (Goodwin et al., 1992). The pathological responses caused by members of the genus *Aspergillus* vary in severity and clinical course and may occur as both primary and secondary infections (Rinaldi, M. G., 1988).

Invasive aspergillosis (IA) is a life-threatening condition in immunocompromised patients, particularly those treated with chemotherapy for hematologic malignancies or those receiving high-dose corticosteroids (Fisher et al., 1981). An early diagnosis of aspergillosis is of great importance because early treatment may resolve this potentially fatal infection. Unfortunately, the diagnosis of IA remains difficult and sometimes is confirmed only at autopsy. At present, a firm diagnosis is established by histological examination of tissue samples obtained during open lung biopsy as well as by detecting the causative pathogenic fungi in clinical samples. Serological tests such as those involving the detection of antibodies for *Aspergillus* species are less helpful because of the poor antibody responses in immunocompromised patients. In addition, the methods used for detecting circulating *Aspergillus* antigens, such as radioimmunoassay, immunoblotting assay, enzyme immunoassay, and the latex agglutination test, have poor sensitivity (Rogers et al., 1990; Sabetta et al., 1985).

Recently, for the diagnosis of IA, PCR has been used to detect DNA specific for *Aspergillus* species in bronchoalveolar lavage (BAL) fluid from patients with IA (Bretage et al., 1995).

Laboratory diagnosis of fungal infections is often problematic. Fungi are often difficult to culture from readily accessible samples, such as patient's urine, blood or sputum. And because fungi are ubiquitous in nature, a single positive culture from urine or sputum is of limited clinical value. The possibility of contamination is always a very real consideration when interpreting laboratory results. A finding of *Aspergillus* in sputum, for example, is in isolation of limited value and must be evaluated in the context of the patient's clinical signs and symptoms. Often tissue biopsies (from lung or brain) are needed for definitive diagnosis and blood cultures should be carried out for all patients. Isolation of yeast—such as *Candida*—from blood is highly predictive of invasive fungal disease. However *Candida* is cultured from blood in less than 20% of patients with disseminated candidiasis.

Because of the limitation of culture techniques many researchers have tried to find specific antibodies against *Candida* and *Aspergillus* in sequence by using the titre of antibodies as diagnostic criterium. However, the sensitivity of these assays is very low—often less than 50%—as many immunocompromised patients have difficulty raising an adequate immune response. Because of its poor sensitivity, immunodiagnosis of fungal infection is not cost-effective. It often gives a false negative result, and may also lead to fungal infections being diagnosed where none exist, leading to the inappropriate administration of antifungal drugs.

Because of the shortcomings of antibody detection, much attention has been directed to tests which detect fungal antigens or metabolites in body fluids. A major problem is the transient nature of antigens in serum. For most antigen detection tests the overall sensitivity is unacceptably low, although multiple serum sampling somewhat improves detection of antigenaemia.

Moreover, none of the above-cited methods allows, the identification of the fungus up to the species level. Efficient treatment regimens of fungal diseases require a correct identification of the fungus at the species level. For example, certain *Candida* species such as *C. glabrata* and *C. krusei* are less susceptible to the classical azole drugs.

The diagnostics of mycoses is an area where there is a great need for new sophisticated techniques. As already seen in virology and to some degree in bacteriology, the use of specific DNA probes, accompanied by DNA or RNA amplification systems, for the diagnosis of fungal infection may prove useful, and may revolutionize laboratory diagnosis and management of patients with serious fungal disease.

Recently, several methods for detection of fungal pathogens using DNA technology have been described. Genes encoding the rRNA, especially the 18S and 28S rRNA genes, have been frequently used as a target for developing species specific probes (e.g. U.S. Pat. No. 5,827,651; Einsele et al. 1997). Others report on the use of the Internal Transcribed Spacer (ITS) region, located in between the 18S and 28S rRNA genes, as a target region for the specific detection of fungi. Lu et al. (1995) describe the subtyping of *Pneumocystis carinii* strains using probes originating from the ITS region. Williams et al. (1995) demonstrate identification of *Candida* species by PCR amplification and restriction length polymorphism analysis of the ITS amplified regions. Kumeda and Asao (1996) use PCR amplification and single strand conformation polymorphism (sscp) analysis of the ITS region to differentiate species of *Aspergillus*. U.S. Pat. No. 5,693, 501 describes specific primers originating from the ITS-1 region for detection of *Histoplasma capsulatum*. A number of patent applications (WO98/50584; WO95/29260; U.S. Pat. No. 5,814,463; U.S. Pat. No. 5,955,274) describe detection and differentiation of different plant fungal pathogens based on specific amplification of or hybridization to ITS-region sequences.

Detection of *Candida* species based on ITS-2 region sequences has been described by several groups. Fujita et al. (1995) describe ITS-2 probes for different *Candida* species and methods for detection and differentiation after a general amplification step with universal primers ITS3 and ITS4. Elie et al. (1998) and several related patent applications (WO98/11257; WO99/06596; U.S. Pat. No. 5,426,027) describe a set of 18 *Candida* species probes originating from the ITS-2 region. Shin et al. (1999) describe detection and differentation of three *Candida* species in a single reaction tube, using amplification with the universal primers ITS3 and ITS4 and hybridization to ITS-2 probes. Botelho and Planta (1994) describe probes for *Candida albicans*, derived from the ITS-1 or ITS-2 regions. The ITS-2 region probes show a better species specificity.

Species specific probes originating from the ITS-region of other medically important fungal species, such as species belonging to *Aspergillus, Cryptococcus*, or *Pneumocystis* have not been described yet. Moreover, methods for simultaneous detection and differentiation of a wide variety of fungal species with clinical importance have not been described yet. Such methods would provide an answer to the need for rapid, highly sensitive and species specific detection of fungal pathogens in clinical samples, allowing a quick installment of efficient treatment regimens, and close monitoring of a patient's progression.

SUMMARY AND AIMS OF THE INVENTION

The present invention describes nucleic acid molecules (oligonucleotide probes) hybridizing specifically with the ITS region of different fungal species with clinical importance. More particularely, probes are described hybridizing selectively with the ITS-1 and/or ITS-2 region of several *Candida* species, *Aspergillus* species, *Cryptococcus neoformans* and *Pneumocystis carinii*. The most preferred probes of the current invention are located in the ITS-1 region, which separates the 18S and 5.8S rRNA genes.

In addition, methods are described for quick sensitive and specific detection and differentiation of these fungal pathogenic species, in particular, methods are described for the simultaneous detection and differentiation of different fungal species in one single hybridization assay. Such multi parameter detection methods may be particularly useful in the detection of opportunistic infections in patients with impaired immunity systems, such as organ transplant patients, patients receiving intensive anticancer treatments, diabetics or AIDS patients.

The methods and probes described are useful tools in clinical diagnosis of fungal infections. Moreover, they may be used to monitor the disease and to guide an appropriate antifungal therapy. The probes and methods described may also be used as laboratory research tools to study the different fungal organisms, and their phylogenetic relationship.

The fungal species detected and identified by the probes and methods of the invention include *Candida albicans, Candida parapsilosis, Candida tropicalis, Candida kefyr, Candida krusei, Candida glabrata, Candida dubliniensis, Aspergillus flavus, Aspergillus versicolor, Aspergillus nidulans, Aspergillus fumigatus, Cryptococcus neoformans* and *Pneumocystis carinii*. The methods of the current invention allow to detect any of the aforementioned species either alone, or in combination with each other, depending on the set of probes applied in the method. All probes are designed such that they are functional under identical hybridization conditions, thus allowing any possible combination. The particular set of probes combined in a given method may depend on several ad hoc parameters, such as: the type of sample (respiratory tract, urogenitary tract, gastrointestinal tract, cerebrospinal fluid, blood samples, skin or tissue biopsies . . . ), the clinical symptoms of the patient, the desired level of specificity (genus, species, strain), the type of application (screening assay, confirmation assay, therapy monitoring, research tool for strain characterization, epidemiology . . . ).

It is thus an object of the current invention to provide nucleic acid probes and primers for the specific detection and identification of several fungal pathogens of clinical importance.

More particularly, it is an object of the current invention to provide nucleic acid probes hybridizing specifically to the ITS (Internal Transcribed Spacer) region of different fungal pathogens. The probes disclosed in the current invention hybridize to the ITS-1 or ITS-2 region, most preferably to the ITS-1 region.

In particular, it is an object of the current invention to provide probes for the detection and identification of several *Candida* species, including *C. albicans, C. parapsilosis, C. tropicalis, C. kefyr, C. krusei, C. glabrata* and *C. dubliniensis*, of several *Aspergillus* species, including *A. flavus, A. versicolor, A. nidulans* and *A. fumigatus*, of *Cryptococcus neoformans* and *Pneumocystis carinii*.

In addition, it is an object of the current invention to provide quick, sensitive and specific methods to detect and identify these fungal pathogens in clinical samples or in cultures.

It is also an object of the current invention to provide for a quick and efficient treatment method of blood samples, resulting in a release of the nucleic acids from fungal cells present in the blood sample, and a removal of possible PCR inhibitors present in the blood sample.

It is furthermore an object of the present invention to provide methods which enable a simultaneous detection and identification of these fungal species possibly present in a sample, in one single assay.

It is also an aim of the present invention to provide methods for clinical diagnosis, monitoring and therapeutic managing of fungal diseases.

These and other objects, including specific advantages and features of the current invention will become apparent in the detailed description of the several embodiments hereafter.

DEFINITIONS

The term "probe" refers to isolated single stranded sequence-specific oligonucleotides which have a sequence which is complementary to the target sequence to be detected. Complementarity of the probe sequence to the target sequence is essential and complete for the central part of the probe (=core of the probe), where no mismatches to the target sequence are allowed. Towards the extremities (3' or 5') of the probe, minor variations in the probe sequence may sometimes occur, without affecting the species specific hybridization behaviour of the probe. The "core sequence" of the probe is the central part, and represents more than 70%, preferably more than 80%, most often more than 90% of the total probe sequence.

The probes of the current invention specifically hybridize to the fungal species for which they are designed. This species specific hybridization behaviour will be illustrated amply; in the examples section. Throughout this invention, the sequences of the probes are always represented from the 5' end to the 3' end. They are represented as single stranded DNA molecules. It should be understood however that these probes may also be used in their RNA form (wherein T is replaced by U), or in their complementary form.

The probes of the current invention may be formed by cloning of recombinant plasmids containing inserts comprising the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phospho-triester method.

Preferably, the probes of the current invention have a length from about 10 to about 30 nucleotides. Variations are possible in the length of the probes and it should be clear that, since the central part of the probe is essential for its hybridization characteristics, possible deviations of the probe sequence versus the target sequence may be allowable towards head and tail of the probe, especially when longer probe sequences are used. These variant probes, which may be conceived from the common knowledge in the art, should however always be evaluated experimentally, in order to check if they result in equivalent hybridization characteristics than the original probes.

The term "isolated" as used herein means that the oligonucleotides of the current invention are isolated from the environment in which they naturally occur. In particular, it means that they are not an % more part of the genome of the respective fungal species, and thus liberated from the remaining flanking nucleotides in the ITS region of said fungal species. On the contrary, new (=heterologous) flanking regions may be added to the 3' and/or 5' end of the probe, in order to enhance its functionality. Functional characteristics possibly provided by said heterologous flanking sequences are e.g. ease of attachment to a solid support, ease of synthesis, ease of purification, labelling function etc.

The term "complementary" nucleic acid as used in the current invention means that the nucleic acid sequences can form a perfect base-paired double helix with each other.

The term "species specific hybridization" refers to a selective hybridization of the probes of the invention to the nucleic acids of the species to be detected (=target organism), and not to nucleic acids originating from strains belonging to other species (=non-target organisms). Species specific hybridization in the context of the present invention also implies a selective hybridization of the probes of the invention to the ITS region (=target region) of the organism to be detected, and limits occasional "random" hybridization to other genomic sequences. Species specificity is a feature which has to be experimentally determined. Although it may sometimes be theoretically predictable, species specificity can only refer to those non-target organisms which have been tested experimentally.

The term "primer" refers to an isolated single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5-50 nucleotides long, more preferably from 10 to 40 nucleotides long. Specific length and sequence will depend on the complexity of the required DNA or RNA targets, as well as on the conditions of primer use such as temperature and ionic strength.

The oligonucleotides used as primers or probes may also comprise nucleotide analogues such as phosphorothiates (Matsukura et al., 1987), alkylphosphorothiates (Miller et al. 1979) or peptide nucleic acids (Nielsen et al., 1991; Nielsen et al., 1993) or may contain intercalating agents (Asseline et al., 1984).

As most other variations or modifications introduced into the original DNA sequences of the invention, these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The term "sample" represents any material possibly containing fungal nucleic acids, which may have to be released from the cells. Preferably, the term "sample" refers to a clinical sample, such as a sample taken from blood, from the respiratory tract (sputum, bronchoalveolar lavage (BAL)), from cerebrospinal fluid (CSF), from the urogenital tract (vaginal secretions, urine), from the gastrointestinal tract (saliva, faeces) or biopsies taken from organs, tissue, skin e.a. The term "sample" may also refer to a sample of cultured fungal cells, either cultured in liquid medium or on solid growth media. Fungal DNA present in said samples may be prepared or extracted according to any of the techniques known in the art.

The term "ITS" is the abbreviated term for Internal Transcribed Spacer region located between the 18S and the 28S rRNA genes in the rRNA operon of the fungal species' nuclear DNA (for a review, see White et al. 1990). The ITS region is subdivided in the ITS-1 region, which separates the 18S and 5.8S rRNA genes, and the ITS-2 region which is found between the 5.8S and 28S rRNA genes.

The "target" material in these samples may be either genomic DNA or precursor ribosomal RNA of the organism to be detected (=target organism), or amplified versions thereof. These molecules are called target nucleic acids. More specifically, the target nucleic acid in the genome is the Internal Transcribed Spacer region (ITS). According to a preferred embodiment, the target region in the genome is the ITS-1 region. The target sequence is that part of the ITS sequence which is fully complementary to the core part of the probe.

DETAILED DESCRIPTION OF THE INVENTION

The present invention provides in its most general form for a method to detect and identify fungal pathogenic species in a sample, comprising at least the following steps:

(i) releasing, isolating and/or concentrating the nucleic acids of the fungal pathogens possibly present in the sample, (ii) if necessary, amplifying the Internal Transcribed Spacer region (ITS) of said nucleic acids with at least one fungal universal primer pair, (iii) hybridizing the nucleic acids of step (i) or (ii) with at least one probe selected from the following group of species specific oligonucleotide probes:

| Sequence | SEQ ID |
|---|---|
| GTCTAAACTTACAACCAATT, | (SEQ ID NO 1) |
| TGTCACACCAGATTATTACT, | (SEQ ID NO 2) |
| TATCAACTTGTCACACCAGA, | (SEQ ID NO 3) |
| GTAGGCCTTCTATATGGG, | (SEQ ID NO 4) |
| TGCCAGAGATTAAACTCAAC, | (SEQ ID NO 5) |
| GGTTATAACTAAACCAAACT, | (SEQ ID NO 6) |
| TTTTCCCTATGAACTACTTC, | (SEQ ID NO 7) |
| AGAGCTCGTCTCTCCAGT, | (SEQ ID NO 8) |
| GGAATATAGCATATAGTCGA, | (SEQ ID NO 9) |
| GAGCTCGGAGAGAGACATC, | (SEQ ID NO 10) |
| TAGTGGTATAAGGCGGAGAT, | (SEQ ID NO 11) |
| CTAAGGCGGTCTCTGGC, | (SEQ ID NO 12) |
| GTTTTGTTCTGGACAAACTT, | (SEQ ID NO 13) |
| CTTCTAAATGTAATGAATGT, | (SEQ ID NO 14) |
| CATCTACACCTGTGAACTGT, | (SEQ ID NO 15) |
| GGACAGTAGAGAATATTGG, | (SEQ ID NO 16) |
| GGACTTGGATTTGGGTGT, | (SEQ ID NO 17) |
| GTTTACTGTACCTTAGTTGCT, | (SEQ ID NO 18) |

-continued

| | |
|---|---|
| CCGCCATTCATGGCC, | (SEQ ID NO 19) |
| CGGGGGCTCTCAGCC, | (SEQ ID NO 20) |
| CCTCTCGGGGCGAGCC, | (SEQ ID NO 21) |
| CCGAGTGCGGCTGCCTC, | (SEQ ID NO 22) |
| CCGAGTGCGGGCTGC, | (SEQ ID NO 23) |
| GAGCCTGAATACCAAATCAG, | (SEQ ID NO 24) |
| GAGCCTGAATACAAATCAG, | (SEQ ID NO 25) |
| GTTGATTATCGTAATCAGT, | (SEQ ID NO 26) |
| GCGACACCCAACTTTATT, | (SEQ ID NO 27) |
| ATGCTAGTCTGAAATTCAAAAG, | (SEQ ID NO 28) |
| GGATTGGGCTTTGCAAATATT, | (SEQ ID NO 29) |
| TTCGCTGGGAAAGAAGG, | (SEQ ID NO 30) |
| GCTTGCCTCGCCAAAGGTG, | (SEQ ID NO 31) |
| TAAATTGAATTTCAGTTTTAGAATT, | (SEQ ID NO 32) |
| TTGTCACACCAGATTATTACTT, | (SEQ ID NO 33) |
| GGTTTATCAACTTGTCACACCAGA, | (SEQ ID NO 34) |
| GGTATCAACTTGTCACACCAGATT, | (SEQ ID NO 35) |
| GGTTATAACTAAACCAAACTTTTT, | (SEQ ID NO 36) |
| GGGAATATAGCATATAGTCGA, | (SEQ ID NO 37) |
| GGTTTTGTTCTGGACAAACTT, | (SEQ ID NO 38) |
| CATCTACACCTGTGAACTGTTT, | (SEQ ID NO 39) |
| CCGACACCCAACTTTATTTTT, | (SEQ ID NO 40) |
| GTTGATTATCGTAATCAGTT, | (SEQ ID NO 41) |
| GAACTCTGTCTGATCTAGT, | (SEQ ID NO 42) |
| GTCTGAATATAAAATCAGTCA, | (SEQ ID NO 43) | or variants of said probes, said variants differing from the sequences cited above by the deletion and/or addition of one or two nucleotides at the 5' and/or 3' extremity of the nucleotide sequence, without affecting the species specific hybridization behaviour of the probe, or the RNA equivalents of said probes, wherein T is replaced by U, or the complementary nucleic acids of said probes, and (iv) detecting the hybridization complexes formed in step (iii).

The probes used in the above described method for detection of fungal pathogens are all hybridizing to the Internal Transcribed Spacer region of fungal species. More particularly, as illustrated further in the examples section (see Table 1), the above-cited probes hybridize selectively to the following target regions: ITS-1 region of *Candida albicans* (probes represented by SEQ ID NO 1, 2, 3, 33, 34, 35), ITS-1 region of *C. parapsilosis* (probes represented by SEQ ID NO 4,5), ITS-1 region of *C. tropicalis* (probes represented by SEQ ID NO 6, 36). ITS-1 region of *C. kefyr* (probes represented by SEQ ID NO 7, 8), ITS-1 region of *C. krusei* (probes represented by SEQ ID NO 9, 37), ITS-1 region of *C. glabrata* (probes represented by SEQ ID NO 10), ITS-1 region of *C. dubliniensis* (probes represented by SEQ ID NO 13, 38), ITS-2 region of *C. dubliniensis* (probes represented by SEQ ID NO 11, 12), ITS-1 region of *Cryptococcus neoformans* (probes represented by SEQ ID NO 14, 15, 16, 39), ITS-2 region of *Cryptococcus neoformans* (probes represented by SEQ ID NO 17), ITS-1 region of *Aspergillus flavus* (probes represented by SEQ ID NO 18, 19, 20, 42), ITS-1 region *Aspergillus versicolor* (probes represented by SEQ ID NO 21, 43), ITS-1 region of *Aspergillus nidulans* (probes represented by SEQ ID NO 22, 23, 24, 25), ITS-1 region of *Aspergillus fumigatus* (probes represented by SEQ ID NO 26, 41), ITS-2 region of *Aspergillus fumigatus* (probes represented by SEQ ID NO 27, 40), ITS-1 region of *Pneumocystis carinii* (probes represented by SEQ ID NO 31, 32), and ITS-2 region of *Pneumocystis carinii* (probes represented by SEQ ID NO 28, 29, 30).

The expression "variants" of the probes encompasses probes represented by a variant sequence which differs from any of the sequences cited above by the deletion and/or addition of 1 or 2 nucleotides at the 3' and/or 5' extremity of the probe sequence, in so far as such deletion or addition does not change the species specific character of the respective probe. It will be understood that the addition of 1 or 2 nucleotides at the extremities of the probes will usually be done in accordance with the sequence flanking the target sequence in the ITS region from which the probe is isolated. This means that one shall normally not choose "any" nucleotide to extend the probe sequence, but only those nucleotides which are flanking the probe sequence in the ITS region. The information about the flanking sequences of the probes can easily be obtained by aligning the probe sequence to the ITS sequence. The ITS sequence itself may be obtained by sequencing the ITS region, after cloning or e.g. PCR amplification of the ITS region with fungal universal primer pairs, or may be retrieved from publicly available sources.

The probes and variant probes as above described may also be extended at the 3' and/or 5' end with non-ITS (=heterologous) flanking sequences. Without affecting the intrinsic hybridization behaviour of the probe, this heterologous tailing process may provide some additional characteristics to the probe molecule, such as e.g. adhesion to a surface by polyT tailing, as described furtheron in the examples section.

The above-described method may be applied for the detection of one single fungal species, so called "single analyte detection", e.g. in microtiter plates, or for the detection of several fungal species simultaneously, so called "multi parameter detection", e.g. in a Line Probe Assay (LiPA). The probes described have been selected such that they may all be functional (i.e. show the desired species specificity) under the same hybridization and wash conditions. This allows the method to be used for the simultaneous detection and differentiation of several fungal species in one single hybridization assay.

The term "fungal universal primer pair" means that the primer pair amplifies the Internal Transcribed Spacer region of most, if not all, fungal species. The sequences of "fungal universal primer pairs" are phylogenetically conserved in order to enable amplification within different species of fungi. They are located in the rRNA genes flanking the ITS region, i.e. in the 18S, 5.8S or 28S rRNA genes. Amplification of the full ITS region, the ITS-1 or the ITS-2 region may be envisaged. "Fungal universal primer pairs" suitable for the methods described in the current invention have been described by a. o. White et al. (1990).

In a preferred embodiment, the method described above includes an amplification step using a fungal universal primer pair which is chosen from the following group of primer pairs, as described by White et al. (1990):

```
ITS5 (forward):
GGAAGTAAAAGTCGTAACAAGG
(SEQ ID NO:44)
and

ITS4 (reverse):
TCCTCCGCTTATTGATATGC,
(SEQ ID NO:45)

ITS5 (forward):
GGAAGTAAAAGTCGTAACAAGG
(SEQ ID NO:44)
and

ITS2 (reverse):
GCTGCGTTCTTCATCGATGC,
(SEQ ID NO:46)

ITS1 (forward):
TCCGTAGGTGAACCTGCGG
(SEQ ID NO:47)
and

ITS4 (reverse):
TCCTCCGCTTATTGATATGC,
(SEQ ID NO:45)

ITS1 (forward):
TCCGTAGGTGAACCTGCGG
(SEQ ID NO:47)
and

ITS2 (reverse):
GCTGCGTTCTTCATCGATGC,
(SEQ ID NO:48)

ITS3 (forward):
GCATCGATGAAGAACGCAGC
(SEQ ID NO:49)
and

ITS4 (reverse):
TCCTCCGCTTATTGATATGC.
(SEQ ID NO:45)
```

The full ITS region may be amplified using a combination of the ITS1 and ITS4 primer, or the ITS-5 and ITS4 primer. The ITS-1 region may be amplified using a combination of the ITS1 and ITS2 primer, or the ITS5 and ITS1 primer, while the ITS-2 region may be amplified using a combination of the ITS3 and ITS4 primer.

According to a preferred embodiment, amplification of the ITS-1 region is envisaged, and probes will be chosen from the ITS-1 region. As will be shown further on in the examples section, the current invention shows that methods based on amplification of and hybridization to the ITS-1 region usually show a higher sensitivity than methods based on amplification of and hybridization to the full ITS region, or the ITS-2 amplified region. The present invention furthermore shows that identification and differentiation of most, if not all, of the different fungal species listed can be accomplished by using probe sequences originating from the ITS-1 region only.

Thus, according to a preferred embodiment, the present invention provides for a method for the detection and identification of fungal pathogenic species in a sample, comprising at least the following steps:

(i) releasing, isolating and or concentrating the nucleic acids of the fungal pathogens possibly present in the sample.

(ii) amplifying the ITS-1 region of said nucleic acids with at least one of the following primer pairs according to s-Mite et al. (1990): (ITS5 and ITS2) or (ITS1 and ITS2), (iii) hybridizing the nucleic acids of step (i) or (ii) with at least one probe selected from the following group of species specific oligonucleotide probes:

| Sequence | ID |
|---|---|
| GTCTAAACTTACAACCAATT, | (SEQ ID NO 1) |
| TGTCACACCAGATTATTACT, | (SEQ ID NO 2) |
| TATCAACTTGTCACACCAGA, | (SEQ ID NO 3) |
| GTAGGCCTTCTATATGGG, | (SEQ ID NO 4) |
| TGCCAGAGATTAAACTCAAC, | (SEQ ID NO 5) |
| GGTTATAACTAAACCAAACT, | (SEQ ID NO 6) |
| TTTTCCCTATGAACTACTTC, | (SEQ ID NO 7) |
| AGAGCTCGTCTCTCCAGT, | (SEQ ID NO 8) |
| GGAATATAGCATATAGTCGA, | (SEQ ID NO 9) |
| GAGCTCGGAGAGAGACATC, | (SEQ ID NO 10) |
| GTTTTGTTCTGGACAAACTT, | (SEQ ID NO 13) |
| CTTCTAAATGTAATGAATGT, | (SEQ ID NO 14) |
| CATCTACACCTGTGAACTGT, | (SEQ ID NO 15) |
| GGACAGTAGAGAATATTGG, | (SEQ ID NO 16) |
| GTTTACTGTACCTTAGTTGCT, | (SEQ ID NO 18) |
| CCGCCATTCATGGCC, | (SEQ ID NO 19) |
| CGGGGGCTCTCAGCC, | (SEQ ID NO 20) |
| CCTCTCGGGGGCGAGCC, | (SEQ ID NO 21) |
| CCGAGTGCGGCTGCCTC, | (SEQ ID NO 22) |
| CCGAGTGCGGGCTGC, | (SEQ ID NO 23) |
| GAGCCTGAATACCAAATCAG, | (SEQ ID NO 24) |
| GAGCCTGAATACAAATCAG, | (SEQ ID NO 25) |
| GTTGATTATCGTAATCAGT, | (SEQ ID NO 26) |
| GCTTGCCTCGCCAAAGGTG, | (SEQ ID NO 31) |
| TAAATTGAATTTCAGTTTTAGAATT, | (SEQ ID NO 32) |
| TTGTCACACCAGATTATTACTT, | (SEQ ID NO 33) |
| GGTTTATCAACTTGTCACACCAGA, | (SEQ ID NO 34) |
| GGTATCAACTTGTCACACCAGATT, | (SEQ ID NO 35) |
| GGTTATAACTAAACCAAACTTTTT, | (SEQ ID NO 36) |
| GGGAATATAGCATATAGTCGA, | (SEQ ID NO 37) |
| GGTTTTGTTCTGGACAAACTT, | (SEQ ID NO 38) |
| CATCTACACCTGTGAACTGTTT, | (SEQ ID NO 39) |
| GTTGATTATCGTAATCAGTT, | (SEQ ID NO 41) |
| GAACTCTGTCTGATCTAGT, | (SEQ ID NO 42) |
| GTCTGAATATAAAATCAGTCA, | (SEQ ID NO 43) | or variants of said probes, said variants differing from the sequences cited above by the deletion and/or addition of one or two nucleotides at the 5' and/or 3' extremity of the nucleotide sequence, without affecting the species specific hybridization behaviour of the probe, or the RNA equivalents of said probes, wherein T is replaced by U, or the complementary nucleic acids of said probes, and
(iv) detecting the hybridization complexes formed in step (iii).

Amplification of the nucleic acids may be carried out according to any method known in the art, including the polymerase chain reaction (PCR; Saiki et al., 1988), ligase chain reaction (LCR; Landgren et al., 1988), nucleic acid sequence-based amplification (NASBA; Guatelli et al., 1990), transcription-based amplification system (TAS; Kwoh et al., 1989), strand displacement amplification (SDA; Duck, 1990) or amplification by means of Qβ replicase (Lomeli et al., 1989) or any other suitable method to amplify nucleic acid molecules know-n in the art.

Amplification of the nucleic acids to be detected has of course the advantage of increasing the sensitivity of detection. Moreover, using fungal universal primer pairs, methods for simultaneous detection can be developed including simultaneous amplification of the ITS region of several fungal species, followed by species specific hybridization. Amplification also allows the incorporation of a label into the amplified nucleic acids, which opens different ways of detecting the hybridization complexes formed, and which may increase the sensitivity of detection again. Labelling may be carried out by the use of labelled nucleotides incorporated during the polymerase step of the amplification such as illustrated by e.g. Bej et al. (1990) or labelled primers, or by any other method known to the person skilled in the art. The nature of the label may be isotopic ($^{32}P$, $^{35}S$, etc.) or non-isotopic (biotin, digoxigenin, fluorescein etc.). Alternatively, of course; the probes of the invention may be labelled.

Hybridization of the nucleic acids is carried out according to standard methods. Preferably, stringent hybridization conditions are used. i.e. conditions enabling differentiation by hybridization between nucleic acids which differ by only one single nucleotide. Examples of stringent conditions applicable to the probes of the current invention are a hybridization buffer of 2×SSC (Sodium Saline Citrate) and 0.1% SDS at a hybridization temperature of 50° C. All probes of the current invention are designed such that they show the desired (=species specific) hybridization behaviour at stringency conditions defined by a hybridization medium of 2×SSC and 0.1% SDS and a hybridization temperature of 50° C. Any other hybridization condition (i.e. any other combination of hybridization buffer and hybridization temperature) resulting in the same degree of stringency is of course also suitable for the probes of the current invention. The design of hybridization conditions to meet certain stringency criteria is common knowledge in the art of hybridization.

Hybridization may be carried out in solution or on a solid support, with either the probes being immobilized to the solid support or the nucleic acids to be detected being immobilized. Immobilization of the nucleic acids to a solid support may be done covalently, or using non-covalent binding forces.

According to a preferred embodiment, the oligonucleotide probes of the invention are immobilized to a solid support, and reverse hybridization is carried out.

The term "solid support" in the current invention refers to any substrate to which an oligonucleotide probe can be coupled, provided that its hybridization characteristics are retained and provided that the background of hybridization remains low. Usually the solid support will be a microtiter plate, a membrane (e.g. nylon or nitrocellulose) or a microsphere (bead). Prior to application to the membrane or fixation it may be convenient to modify the nucleic acid probe in order to facilitate fixation or to improve the hybridization efficiency. Such modifications may encompass homopolymer tailing, coupling with different reactive groups such as aliphatic groups, NH2 groups, SH groups, carboxylic groups, or coupling with biotin, haptens or proteins.

According to a preferred embodiment, the oligonucleotides used in the above described methods of detection are immobilized to a solid support by means of a homopolymer tailing sequence (e.g. polyT) which is added at the 3' or 5' extremity of the probe. Said tailing may be done during chemical synthesis of the oligonucleotide, usually resulting in a 5' polyT tail, or afterwards, e.g. via enzymatic tailing using terminal deoxynucleotidyl transferase (Pharmacia), resulting in a 3' polyT tail.

Detection of the hybridization complexes formed may be done according to any methods known in the art, the type of detection of course depending on the type of label used. When biotin is used as a label, streptavidin conjugated detection agents may be used, such as e.g. streptavidin conjugated alkaline phosphatase, causing a blue precipitation signal, or streptavidin conjugated horse raddish peroxidase, causing a color reaction in solution.

According to a special embodiment, the invention provides for a LiPA (Line Probe Assay) method for detecting and identifying fungal pathogens in a sample, as shown below in the examples section. LiPA is a reverse hybridization assay using oligonucleotide probes immobilized as parallel lines on a solid support strip (as described by Stuyver et al. (1993) and WO 94/12670). LiPA is particularly advantageous since it is fast and simple to perform. Moreover, this method is amenable to automation (Auto-LiPA, Innogenetics, Zwijnaarde, Belgium) and thus particularly suitable for clinical settings where multiple samples can be processed simultaneously. It is to be understood however, that any other type of hybridization assay or format using any of the selected probes as described further, is also covered by the present invention.

According to a preferred embodiment, the method described above may be applied for the simultaneaous detection and differentiation of fungal pathogens present in a particular type of sample. For example, when the sample is a blood or serum sample, the methods of the invention may comprise detection and differentiation of *Candida* species, *Aspergillus* species, and *Cryptococcus* species. When the sample originates from the respiratory tract (e.g. sputum samples, BAL samples) the methods of the current invention may comprise detection and differentiation of *Candida* species, most often species other than *Candida albicans*. *Aspergillus* species, *Cryptococcus* species and *Pneumocystis carinii*. When the sample originates from CSF, the methods of the invention may comprise detection and differentiation of *Candida* species, *Aspergillus* species, *Cryptococcus* species and *Pneumocystis carinii*. When the sample originates from skin or wound tissue, the methods of the invention may comprise detection and differentiation of *Aspergillus* species, *Candida* species, *Cryptococcus* species. When the sample originates from the urogenital tract, the methods of the invention enable detection and differentiation of different types of *Candida* species.

According to a more specific embodiment, the current invention provides for a method as described above, wherein said fungal pathogen is a *Candida* species, and wherein the probes of step (iii) are chosen from among SEQ ID NO 1, 2, 3, 33, 34 and 35 for *C. albicans*, SEQ ID NO 4 and 5 for *C. parapsilosis*, SEQ ID NO 6 and 36 for *C. tropicalis*. SEQ ID NO 7 and 8 for *C. kefyr*, SEQ ID NO 9 and 37 for *C. krusei*, SEQ ID NO 10 for *C. glabrata*, and SEQ ID NO 11, 12, 13 and 38 for *C. dubliniensis*.

According to a more specific embodiment, the current invention provides for a method to detect *Candida albicans* in a sample, said method including (i) hybridizing the nucleic acids present in the sample to at least one of the probes represented by SEQ ID NO 1, 2, 3, 33, 34 and 35, and (ii) detecting the hybridization complexes formed, the presence of said hybridization complexes being indicative for the presence of *C. albicans*.

According to another specific embodiment, the current invention provides for a method to detect *Candida parapsilosis* in a sample, said method including (i) hybridizing the nucleic acids present in the sample to at least one of the probes represented by SEQ ID NO 4 and 5, and (ii) detecting the hybridization complexes formed, the presence of said hybridization complexes being indicative for the presence of *C. parapsilosis*.

According to another specific embodiment, the current invention provides for a method to detect *Candida tropicalis* in a sample, said method including (i) hybridizing the nucleic acids present in the sample to at least one of the probes represented by SEQ ID NO 6 and 36, and (ii) detecting the hybridization complexes formed, the presence of said hybridization complexes being indicative for the presence of *C. tropicalis*.

According to another specific embodiment, the current invention provides for a method to detect *Candida kefyr* in a sample, said method including (i) hybridizing the nucleic acids present in the sample to at least one of the probes represented by SEQ ID NO 7 and 8, and (ii) detecting the hybridization complexes formed, the presence of said hybridization complexes being indicative for the presence of *C. kefyr*.

According to another specific embodiment, the current invention provides for a method to detect *Candida krusei* in a sample, said method including (i) hybridizing, the nucleic acids present in the sample to at least one of the probes represented by SEQ ID NO 9 and 37, and (ii) detecting the hybridization complexes formed, the presence of said hybridization complexes being indicative for the presence of *C. krusei*.

According to another specific embodiment, the current invention provides for a method to detect *Candida glabrata* in a sample, said method including (i) hybridizing the nucleic acids present in the sample to a probe represented by SEQ ID NO 10, and (ii) detecting the hybridization complexes formed, the presence of said hybridization complexes being indicative for the presence of *C. glabrata*.

According to another specific embodiment, the current invention provides for a method to detect *Candida dubliniensis* in a sample, said method including (i) hybridizing the nucleic acids present in the sample to at least one of the probes represented by SEQ ID NO 11, 12, 13 and 38 and (ii) detecting the hybridization complexes formed, the presence of said hybridization complexes being indicative for the presence of *C. dubliniensis*.

According to a further embodiment, the current invention provides for a method to detect and identify fungal pathogenic species as described above, wherein said fungal pathogen is an *Aspergillus* species, and wherein the probes of step (iii) are chosen from among SEQ ID NO 18, 19, 20 and 42 for *A. flavus*, SEQ ID NO 21 and 43 for *A. versicolor*, SEQ ID NO 22, 23, 24 and 25 for *A. nidulans*, and SEQ ID NO 26, 27, 40 and 41 for *A. fumigatus*.

According to a more specific embodiment, the current invention provides for a method to detect *Aspergillus flavus* in a sample, said method including (i) hybridizing the nucleic acids present in the sample to at least one of the probes represented by SEQ ID NO 18, 19, 20 and 42, and (ii) detecting the hybridization complexes formed, the presence of said hybridization complexes being indicative for the presence of *A. flavus*.

According to another specific embodiment, the current invention provides for a method to detect *Aspergillus versicolor* in a sample, said method including (i) hybridizing the nucleic acids present in the sample to at least one of the probes represented by SEQ ID NO 21 and 43, and (ii) detecting the hybridization complexes formed, the presence of said hybridization complexes being indicative for the presence of *A. versicolor*.

According to another specific embodiment, the current invention provides for a method to detect *Aspergillus nidulans* in a sample, said method including (i) hybridizing the nucleic acids present in the sample to at least one of the probes represented by SEQ ID NO 22, 23, 24 and 25, and (ii) detecting the hybridization complexes formed, the presence of said hybridization complexes being indicative for the presence of *A. nidulans*.

According to another specific embodiment, the current invention provides for a method to detect *Aspergillus fumigatus* in a sample, said method including (i) hybridizing the nucleic acids present in the sample to at least one of the probes represented by SEQ ID NO 26, 27, 40 and 41, and (ii) detecting the hybridization complexes formed, the presence of said hybridization complexes being indicative for the presence of *A. fumigatus*.

According to another particular embodiment, the present invention provides for a method to detect *Cryptococcus neoformans* in a sample, including (i) hybridization of the nucleic acids present in the sample to at least one of the probes represented by SEQ ID NO 14, 15, 16, 17, and 39 and (ii) detecting the hybridization complexes formed, the presence of said hybridization complexes being indicative for the presence of *C. neoformans*.

According to another particular embodiment, the present invention provides for a method to detect *Pneumocystis carinii* in a sample, including (i) hybridization of the nucleic acids present in the sample to at least one of the probes represented by SEQ ID NO 28, 29, 30, 31 and 32, and (ii) detecting the hybridization complexes formed, the presence of said hybridization complexes being indicative for the presence of *P. carinii*.

According to a preferred embodiment, the oligonucleotide probes used in the above described methods of detection are immobilized to a solid support.

According to a particularly preferred embodiment, the current invention provides for a method for detection and identification of fungal pathogens in a sample as described above, whereby the amplification of step (ii) is mandatory, and includes the labelling of the nucleic acids to be detected.

According to a particularly advantageous embodiment, the current invention provides for a method for the simultaneous detection and differentiation of at least two fungal pathogenic species in one single assay, including (i) releasing, isolating and/or concentrating the nucleic acids of the fungal pathogens possibly present in the sample, (ii) amplifying the Internal Transcribed Spacer region (ITS) of said nucleic acids with at least one fungal universal primer pair, (iii) hybridizing the nucleic acids of step (i) or (ii) with at least two of the following species specific oligonucleotide probes:

| | |
|---|---|
| GTCTAAACTTACAACCAATT | (SEQ ID NO 1) |
| TGTCACACCAGATTATTACT | (SEQ ID NO 2) |
| TATCAACTTGTCACACCAGA | (SEQ ID NO 3) |
| GTAGGCCTTCTATATGGG | (SEQ ID NO 4) |
| TGCCAGAGATTAAACTCAAC | (SEQ ID NO 5) |
| GGTTATAACTAAACCAAACT | (SEQ ID NO 6) |
| TTTTCCCTATGAACTACTTC | (SEQ ID NO 7) |
| AGAGCTCGTCTCTCCAGT | (SEQ ID NO 8) |
| GGAATATAGCATATAGTCGA | (SEQ ID NO 9) |
| GAGCTCGGAGAGAGACATC | (SEQ ID NO 10) |
| TAGTGGTATAAGGCGGAGAT | (SEQ ID NO 11) |
| CTAAGGCGGTCTCTGGC | (SEQ ID NO 12) |
| GTTTTGTTCTGGACAAACTT | (SEQ ID NO 13) |
| CTTCTAAATGTAATGAATGT | (SEQ ID NO 14) |
| CATCTACACCTGTGAACTGT | (SEQ ID NO 15) |
| GGACAGTAGAGAATATTGG | (SEQ ID NO 16) |
| GGACTTGGATTTGGGTGT | (SEQ ID NO 17) |
| GTTTACTGTACCTTAGTTGCT | (SEQ ID NO 18) |
| CCGCCATTCATGGCC | (SEQ ID NO 19) |
| CGGGGGCTCTCAGCC | (SEQ ID NO 20) |
| CCTCTCGGGGCGAGCC | (SEQ ID NO 21) |
| CCGAGTGCGGCTGCCTC | (SEQ ID NO 22) |
| CCGAGTGCGGGCTGC | (SEQ ID NO 23) |
| GAGCCTGAATACCAAATCAG | (SEQ ID NO 24) |
| GAGCCTGAATACAAATCAG | (SEQ ID NO 25) |
| GTTGATTATCGTAATCAGT | (SEQ ID NO 26) |
| GCGACACCCAACTTTATT | (SEQ ID NO 27) |
| ATGCTAGTCTGAAATTCAAAAG | (SEQ ID NO 28) |
| GGATTGGGCTTTGCAAATATT | (SEQ ID NO 29) |
| TTCGCTGGGAAAGAAGG | (SEQ ID NO 30) |
| GCTTGCCTCGCCAAAGGTG | (SEQ ID NO 31) |
| TAAATTGAATTTCAGTTTTAGAATT | (SEQ ID NO 32) |
| TTGTCACACCAGATTATTACTT, | (SEQ ID NO 33) |
| GGTTTATCAACTTGTCACACCAGA, | (SEQ ID NO 34) |
| GGTATCAACTTGTCACACCAGATT, | (SEQ ID NO 35) |
| GGTTATAACTAAACCAAACTTTTT, | (SEQ ID NO 36) |
| GGGAATATAGCATATAGTCGA, | (SEQ ID NO 37) |
| GGTTTTGTTCTGGACAAACTT, | (SEQ ID NO 38) |
| CATCTACACCTGTGAACTGTTT, | (SEQ ID NO 39) |
| CCGACACCCAACTTTATTTTT, | (SEQ ID NO 40) |
| GTTGATTATCGTAATCAGTT, | (SEQ ID NO 41) |
| GAACTCTGTCTGATCTAGT, | (SEQ ID NO 42) |
| GTCTGAATATAAAATCAGTCA, | (SEQ ID NO 43) | or variants of said probes, said variants differing from the sequences cited above by the deletion and/or addition of one or two nucleotides at the 5' and/or 3' extremity of the nucleotide sequence, without affecting the species specific hybridization behaviour of the probe, or the RNA equivalents of said probes, wherein T is replaced by U, or the complementary nucleic acids of said probes, wherein said probes have been immobilized to a solid support on specific locations, (iv) detecting the hybridization complexes formed in step (iii), (v) identifying the species present in the sample by the location of the hybridization signal on the solid support.

In the above-cited embodiment, the probes of the invention are immobilized on a solid support on specific locations, e.g. as discrete parallel lines or spots on a membrane strip, or in different wells of a microtiter plate. Each location contains a determined amount of at least one species specific probe, and can therefore be considered as a "species specific location". If necessary, several probes hybridizing to the same species may be combined on one single location. By locating the hybridization signal obtained on the solid support, it is thus possible to identify the fungal species present in the sample (step (v) of the above described method).

According to a preferred embodiment, as will be shown in the examples section, the immobilization of the probes to the solid support occurs via the non-covalent binding of a polyT tail which is attached to one of the extremities of the probe. If enzymatic tailing occurs, the polyT tail is added at the 3' end. If synthetic tailing (SGS) occurs, the polyT tail is usually added at the 5' end. Both types of tailing may be applied to the probes of the invention. If a different type of tailing results in a different hybridization behaviour of the probe, the oligonucleotide sequence may have to be adapted slightly. Examples of such slight variations are illustrated in Table 1 furtheron, where a certain type of probe may be mentioned twice: e.g. Calb2 (SEQ ID NO 2) and Calb2 (SGS) (SEQ ID NO 33), the former probe mentioned being functional with a 3' polyT tail, the latter probe being functional with a 5' polyT tail.

According to another embodiment, the current invention also provides for an isolated oligonucleotide molecule having a nucleotide sequence represented by any of the sequences SEQ ID NO 1 to 43, or variants of said probes, said variants differing from the sequences cited above by the deletion and/or addition of one or two nucleotides at the 5' and/or 3' extremity of the nucleotide sequence, without affecting the species specific hybridization behaviour of the probe, or the RNA equivalents of said probes, wherein T is replaced by U, or the complementary nucleic acids of said probes.

Preferred nucleic acids of the invention consist of a nucleotide sequence represented by any of the sequences SEQ ID NO 1-43. As mentioned above, addition and or deletion of 1 or 2 nucleotides at the 5' and/or 3' extremity may result in functional equivalent molecules, which are also encompassed by the current invention. Moreover, as set out above, it may be desirable to modify the nucleic acid probe in order to facilitate fixation or to improve the hybridization efficiency (e.g. homopolymer tailing, coupling with different reactive groups . . . ). Such modified nucleic acid molecules are also part of the current invention.

More in particular, the current invention provides for an isolated oligonucleotide molecule as described above for use as a species specific primer or probe in the detection of one of the following fungal pathogenic species: *Candida albicans, Candida parapsilosis, Candida tropicalis, Candida kefyr, Candida krusei, Candida glabrata, Candida dubliniensis, Aspergillus flavus, Aspergillus versicolor, Aspergillus nidulans, Aspergillus fumigatus, Cryptococcus neoformans* or *Pneumocystis carinii*.

The current invention also provides for a method as described above, wherein the sample is a blood sample, and wherein step (i) includes
  incubation of the blood sample with lysis buffer (10 mM Tris-HCl, ph 7.5, 10 mM EDTA, 50 mM NaCl), followed by centrifugation and removal of the supernatant, and
  vortexing of the resuspended cell pellet in the presence of glass beads.

The above-described sample pretreatment is described in further detail in the examples section, and is shown to be applicable to a wide variety of fungal species.

FIGURE LEGEND

Figure 2:
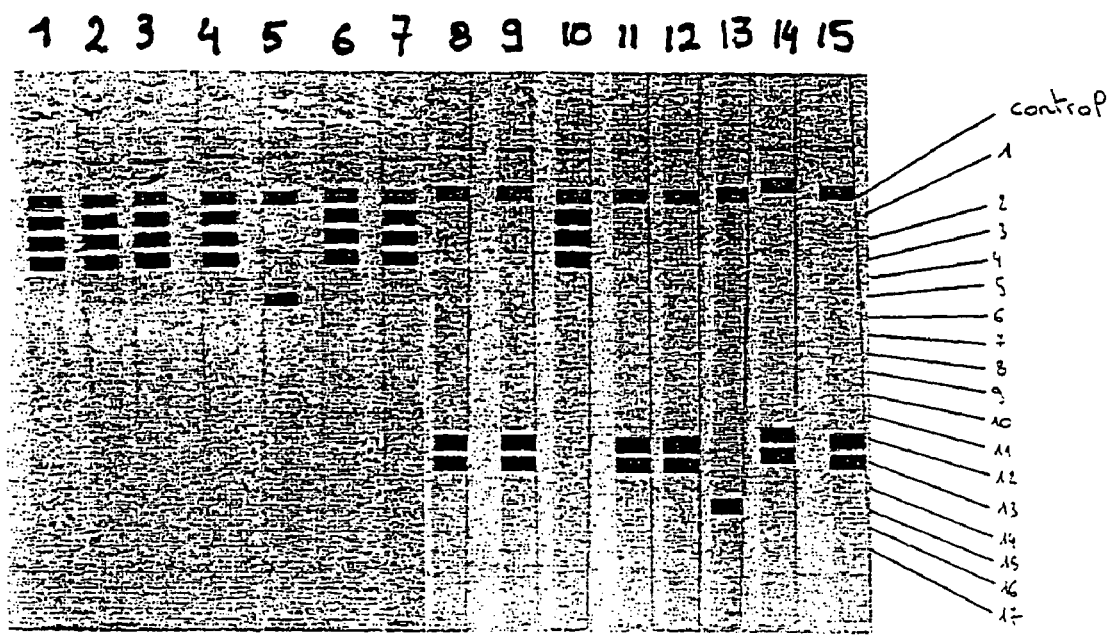

FIG. 1: Hybridization results of full ITS, ITS-1 or ITS-2 amplicons to LiPA strips containing species-specific probes.
  Lanes:
  lane 1: PCR blanc (i.e. no PCR amplicon added to this lane)
  lanes 2,3: *C. albicans* (2: full ITS, 3: ITS-1)
  lanes 4,5: *C. parapsilosis* (4: full ITS, 5: ITS-1)
  lanes 6,7: *C. glabrata* (6: full ITS, 7: ITS-1)
  lanes 8,9: *C. tropicalis* (8: full ITS, 9: ITS-1)
  lanes 10,11: *C. krusei* (10: full ITS, 11: ITS-1)
  lanes 12,13: *C. dubliniensis* (12: full ITS, 13: ITS-2)
  lanes 14,15: *Cr. neoformans* (14: full ITS, 15: ITS-1)
  lanes 16,17: *A. fumigatus* (16: full ITS, 17: ITS-1)
  lanes 18: *A. nidulans* (full ITS)
  lane 19: *A. flavus* (full ITS)
  lane 20: oligo-dA-bio (hybridizes to (poly-T) tail of the immobilized probes)
  Probe Lines:
  colour reaction control line (heterologous biotinylated oligonucleotide)
  row 1: Calb1
  row 2: Calb2
  row 3: Calb3
  row 4: Cpara2
  row 5: Cglab
  row 6: Ctrop
  row 7: Ckrus
  row 8: Cdub1
  row 9: Cdub2
  row 10: Cmeo2
  row 11: Cmeo4
  row 12: Afum1
  row 13: Afum2
  row 14: Anid1
  row 15: Afla1
  row 16: Aver
  row 17: Aver FIG. 2: LiPA evaluation on clinical isolates
  lanes 1-15: different clinical isolates, identified as
  lanes 1-4, 6, 7, 10: *C. albicans*
  lane 5: *C. glabrata*
  lane 8, 9, 11, 12, 14, 15: *A. fumigatus*
  lane 13: *A. flavus*
  rows: see FIG. 1

TABLE 1

ITS probe sequences for fungal detection and differentiation

| Probe | Sequence | SEQ ID NO | Organism | Spacer region |
|---|---|---|---|---|
| Calb1 | GTCTAAACTTACAACCAATT | SEQ ID NO 1 | *Candida albicans* | ITS1 |
| Calb2 | TGTCACACCAGATTATTACT | SEQ ID NO 2 | *Candida albicans* | ITS1 |
| Calb2 (SGS) | TTGTCACACCAGATTATTACTTT | SEQ ID NO 33 | *Candida albicans* | ITS1 |
| Calb3 | TATCAACTTGTCACACCAGA | SEQ ID NO 3 | *Candida albicans* | ITS1 |
| Calb3 (SGS1) | GGTTTATCAACTTGTCACACCAGA | SEQ ID NO 34 | *Candida albicans* | ITS1 |
| Calb3 (SGS2) | GGTATCAACTTGTCACACCAGATT | SEQ ID NO 35 | *Candida albicans* | ITS1 |
| Cpara1 | GTAGGCCTTCTATATGGG | SEQ ID NO 4 | *Candida parapsilosis* | ITS1 |
| Cpara2 | TGCCAGAGATTAAACTCAAC | SEQ ID NO 5 | *Candida parapsilosis* | ITS1 |
| Ctrop | GGTTATAACTAAACCAAACT | SEQ ID NO 6 | *Candida tropicalis* | ITS1 |
| Ctrop (SGS) | GGTTATAACTAAACCAAACTTTTT | SEQ ID NO 36 | *Candida tropicalis* | ITS1 |
| Ckef1 | TTTTCCCTATGAACTACTTC | SEQ ID NO 7 | *Candida kefyr* | ITS1 |
| Ckef2 | AGAGCTCGTCTCTCCAGT | SEQ ID NO 8 | *Candida kefyr* | ITS1 |
| Ckrus | GGAATATAGCATATAGTCGA | SEQ ID NO 9 | *Candida krusei* | ITS1 |
| Ckrus (SGS) | GGGAATATAGCATATAGTCGA | SEQ ID NO 37 | *Candida krusei* | ITS1 |

TABLE 1-continued

ITS probe sequences for fungal detection and differentiation

| Probe | Sequence | SEQ ID NO | Organism | Spacer region |
|---|---|---|---|---|
| Cglab | GAGCTCGGAGAGAGACATC | SEQ ID NO 10 | Candida glabrata | ITS1 |
| Cdub11 | TAGTGGTATAAGGCGGAGAT | SEQ ID NO 11 | Candida dubliniensis | ITS2 |
| Cdub12 | CTAAGGCGGTCTCTGGC | SEQ ID NO 12 | Candida dubliniensis | ITS2 |
| Cdub13 | GTTTTGTTCTGGACAAACTT | SEQ ID NO 13 | Candida dubliniensis | ITS1 |
| Cdub13 (SGS) | GGTTTTGTTCTGGACAAACTT | SEQ ID NO 38 | Candida dubliniensis | ITS1 |
| Crneo1 | CTTCTAAATGTAATGAATGT | SEQ ID NO 14 | Cryptococcus neoformans | ITS1 |
| Crneo2 | CATCTACACCTGTGAACTGT | SEQ ID NO 15 | Cryptococcus neoformans | ITS1 |
| Crneo2 (SGS) | CATCTACACCTGTGAACTGTTT | SEQ ID NO 39 | Cryptococcus neoformans | ITS1 |
| Crneo3 | GGACAGTAGAGAATATTGG | SEQ ID NO 16 | Cryptococcus neoformans | ITS1 |
| Crneo4 | GGACTTGGATTTGGGTGT | SEQ ID NO 17 | Cryptococcus neoformans | ITS2 |
| Afla1 | GTTTACTGTACCTTAGTTGCT | SEQ ID NO 18 | Aspergillus flavus | ITS1 |
| Afla2 | CCGCCATTCATGGCC | SEQ ID NO 19 | Aspergillus flavus | ITS1 |
| Afla3 | CGGGGGCTCTCAGCC | SEQ ID NO 20 | Aspergillus flavus | ITS1 |
| Afla4 | GAACTCTGTCTGATCTAGT | SEQ ID NO 42 | Aspergillus flavus | ITS1 |
| Aver | CCTCTCGGGGGCGAGCC | SEQ ID NO 21 | Aspergillus versicolor | ITS1 |
| Aver3 (SGS) | GTCTGAATATAAAATCAGTCA | SEQ ID NO 43 | Aspergillus versicolor | ITS1 |
| Anid1 | CCGAGTGCGGCTGCCTC | SEQ ID NO 22 | Aspergillus nidulans | ITS1 |
| Anid1A | CCGAGTGCGGGCTGC | SEQ ID NO 23 | Aspergillus nidulans | ITS1 |
| Anid2 | GAGCCTGAATACCAAATCAG | SEQ ID NO 24 | Aspergillus nidulans | ITS1 |
| Anid2A | GAGCCTGAATACAAATCAG | SEQ ID NO 25 | Aspergillus nidulans | ITS1 |
| Afum2 | GTTGATTATCGTAATCAGT | SEQ ID NO 26 | Aspergillus fumigatus | ITS1 |
| Afum2 (SGS) | GTTGATTATCGTAATCAGTT | SEQ ID NO 41 | Aspergillus fumigatus | ITS1 |
| Afum1 | GCGACACCCAACTTTATT | SEQ ID NO 27 | Aspergillus fumigatus | ITS2 |
| Afum1 (SGS) | CCGACACCCAACTTTATTTTT | SEQ ID NO 40 | Aspergillus fumigatus | ITS2 |
| Pear1 | ATGCTAGTCTGAAATTCAAAAG | SEQ ID NO 28 | Pneumocystis carinii | ITS2 |
| Pear2 | GGATTGGGCTTTGCAAATATT | SEQ ID NO 29 | Pneumocystis carinii | ITS2 |
| Pear3 | TTCGCTGGGAAAGAAGG | SEQ ID NO 30 | Pneumocystis carinii | ITS2 |
| Pear4 | GCTTGCCTCGCCAAAGGTG | SEQ ID NO 31 | Pneumocystis carinii | ITS1 |
| Pear5 | TAAATTGAATTTCAGTTTTAGAATT | SEQ ID NO 32 | Pneumocystis carinii | ITS1 |

TABLE 2

Hybridization results obtained with a selection of the probes of the invention applied on a wide variety of fungal species.

| Species | Ref. nr | Calb1 | Calb2 | Calb3 | Cpara2 | Cglab | Ctrop | Ckrus | Cdub11 |
|---|---|---|---|---|---|---|---|---|---|
| *Penicillium* species | | | | | | | | | |
| P. aurantiogriseum | PIL 563 | | | | | | | | |
| P. antiogriseum var. melanoconidium | PIL 333 | | | | | | | | |
| P. expansum | PIL 346 | | | | | | | | |

TABLE 2-continued

Hybridization results obtained with a selection of the probes of the invention applied on a wide variety of fungal species.

| Species | Strain | 1 | 2 | 3 | 4 | 5 | 6 | 7 | 8 |
|---|---|---|---|---|---|---|---|---|---|
| P. verucosum | PIL 781 | | | | | | | | |
| P. verucosum | PIL 115 | | | | | | | | |
| P. verucosum | PIL 25 | | | | | | | | |
| P. hordei | PIL 351 | | | | | | | | |
| P. islanidcum | PIL 778 | | | | | | | | |
| P. marlensii | PIL 9 | | | | | | | | |
| P. ruber | PIL 162 | | | | | | | | |
| *Aspergillus* species | | | | | | | | | |
| A. fumigatus | NCPF 7097 | | | | | | | | |
| A. fumigatus | NCPF 2109 | | | | | | | | |
| A. fumigatus | NCPF 2937 | | | | | | | | |
| A. nidulans | NCPF 7063 | | | | | | | | |
| A. nidulans | PIL 272 | | | | | | | | |
| A. niger | NCPF 2828 | | | | | | | | |
| A. niger | NCPF 2599 | | | | | | | | |
| A. niger | PIL 4 | | | | | | | | |
| A. restriclus | PIL 167 | | | | | | | | |
| A. restriclus | PIL 87 | | | | | | | | |
| A. restriclus | PIL 34 | | | | | | | | |
| A. restriclus | PIL 116 | | | | | | | | |
| A. ochraceus | PIL 253 | | | | | | | | |
| A. candidus | PIL 129 | | | | | | | | |
| A. terreus | PIL 422 | | | | | | | | |
| A. flavus | NCPF 2199 | | | | | | | | |
| A. flavus | PIL 444 | | | | | | | | |
| A. flavus | PIL 512 | | | | | | | | |
| A. flavus | PIL 447 | | | | | | | | |
| A. flavus | PIL 345 | | | | | | | | |
| A. flavus | PIL 378 | | | | | | | | |
| A. flavus | PIL 295 | | | | | | | | |
| A. flavus | PIL 499 | | | | | | | | |
| A. flavus | PIL 480 | | | | | | | | |
| A. flavus | PIL 377 | | | | | | | | |
| A. flavus | PIL 110 | | | | | | | | |
| A. versicolor | PIL 347 | | | | | | | | |
| A. versicolor | PIL 725 | | | | | | | | |
| A. versicolor | PIL 564 | | | | | | | | |
| A. versicolor | PIL 565 | | | | | | | | |
| A. versicolor | PIL 293 | | | | | | | | |
| A. versicolor | PIL 399 | | | | | | | | |
| A. versicolor | PIL 656 | | | | | | | | |
| A. versicolor | PIL 576 | | | | | | | | |
| A. versicolor | PIL 770 | | | | | | | | |
| *Eurotium* species | | | | | | | | | |
| E. amstelodami | PIL 218 | | | | | | | | |
| E. chevalieri | PIL 280 | | | | | | | | |
| *Fusarium* species | | | | | | | | | |
| F. avenicum | PIL 569 | | | | | | | | |
| F. culmorum | PIL 772 | | | | | | | | |
| F. culmorum | PIL 234 | | | | | | | | |
| F. graminearum | PIL 210 | | | | | | | | |
| F. poae | PIL 773 | | | | | | | | |
| F. moniliforme | PIL 450 | | | | | | | | |
| *Candida* species | | | | | | | | | |
| C. albicans | NCPF 3302 | + | + | + | | | | | |
| C. albicans | NCPF 3328 | + | + | + | | | | | |
| C. albicans | NCPF 3345 | + | + | + | | | | | |
| C. albicans | NCPF 3822 | + | + | + | | | | | |
| C. albicans | NCPF 44490 | + | + | + | | | | | |
| C. guillermondii | | | | | | | | | |
| C. krusei | NCPF 3896 | | | | | | | + | |
| C. krusei | NCPF 3922 | | | | | | | + | |
| C. krusei | NCPF 3845 | | | | | | | + | |
| C. parapsilosis | NCPF 3847 | | | | + | | | | |
| C. glabrata | NCPF 3872 | | | | | | + | | |
| C. glabrata | NCPF 3700 | | | | | | + | | |
| C. kefyr | NCPF 3863 | | | | | | | | |
| C. lusitaniae | NCPF 3898 | | | | | | | | |
| C. tropicalis | NCPF 3924 | | | | | + | | | |
| C. dubliniensis | NCPF 3870 CD 36 | | | | | | | | + |

TABLE 2-continued

Hybridization results obtained with a selection of the probes of the invention applied on a wide variety of fungal species.

*Cryptococcus* species

| | |
|---|---|
| *C. neoformans* var. *gatti* | NCPF 3756 |
| *C. neoformans* var. *neoformans* | NCPF 3232 |
| *C. laurentii* | NCPF 3836 |
| *C. albidus* | NCF 3147 |

Other species

| | |
|---|---|
| *Altemaria alternata* | PIL 764 |
| *Monascus tuber* | PIL 48 |

| Species | Cdubl2 | Crneo2 | Crneo4 | Afum1 | Afum2 | Anid | Afla | Aver |
|---|---|---|---|---|---|---|---|---|
| *Penicillium* species | | | | | | | | |
| *P. aurantiogriseum* | | | | | | | | |
| *P. antiogriseum* var. *melanoconidium* | | | | | | | | |
| *P. expansum* | | | | | | | | |
| *P. verucosum* | | | | | | | | |
| *P. verucosum* | | | | | | | | |
| *P. verucosum* | | | | | | | | |
| *P. hordei* | | | | | | | | |
| *P. islanidcum* | | | | | | | | |
| *P. marlensii* | | | | | | | | |
| *P. ruber* | | | | | | | | |
| *Aspergillus* species | | | | | | | | |
| *A. fumigatus* | | | | + | + | | | |
| *A. fumigatus* | | | | + | + | | | |
| *A. fumigatus* | | | | + | + | | | |
| *A. nidulans* | | | | | | + | | |
| *A. nidulans* | | | | | | + | | |
| *A. niger* | | | | | | | | |
| *A. niger* | | | | | | | | |
| *A. niger* | | | | | | | | |
| *A. restriclus* | | | | | | | | |
| *A. restriclus* | | | | | | | | |
| *A. restriclus* | | | | | | | | |
| *A. restriclus* | | | | | | | | |
| *A. ochraceus* | | | | | | | | |
| *A. candidus* | | | | | | | | |
| *A. terreus* | | | | | | | | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. flavus* | | | | | | | + | |
| *A. versicolor* | | | | | | | | + |
| *A. versicolor* | | | | | | | | + |
| *A. versicolor* | | | | | | | | + |
| *A. versicolor* | | | | | | | | + |
| *A. versicolor* | | | | | | | | + |
| *A. versicolor* | | | | | | | | + |
| *A. versicolor* | | | | | | | | + |
| *A. versicolor* | | | | | | | | + |
| *A. versicolor* | | | | | | | | + |
| *Eurotium* species | | | | | | | | |
| *E. amstelodami* | | | | | | | | |
| *E. chevalieri* | | | | | | | | |
| *Fusarium* species | | | | | | | | |
| *F. avenicum* | | | | | | | | |
| *F. culmorum* | | | | | | | | |
| *F. culmorum* | | | | | | | | |
| *F. graminearum* | | | | | | | | |

TABLE 2-continued

Hybridization results obtained with a selection of the probes of the invention applied on a wide variety of fungal species.

| Species | | | |
|---|---|---|---|
| *F. poae* | | | |
| *F. moniliforme* | | | |
| Candida species | | | |
| | | | |
| *C. albicans* | | | |
| *C. albicans* | | | |
| *C. albicans* | | | |
| *C. albicans* | | | |
| *C. albicans* | | | |
| *C. guillermondii* | | | |
| *C. krusei* | | | |
| *C. krusei* | | | |
| *C. krusei* | | | |
| *C. parapsilosis* | | | |
| *C. glabrata* | | | |
| *C. glabrata* | | | |
| *C. kefyr* | | | |
| *C. lusitaniae* | | | |
| *C. tropicalis* | | | |
| *C. dubliniensis* | + | | |
| Cryptococcus species | | | |
| | | | |
| *C. neoformans* var. *gatti* | | + | + |
| *C. neoformans* var. *neoformans* | | + | + |
| *C. laurentii* | | | |
| *C. albidus* | | | |
| Other species | | | |
| | | | |
| *Alternaria alternata* | | | |
| *Monascus tuber* | | | |

(+) = positive hybridization signal,
( ) = no signal detected

EXAMPLES

1. Specificity Testing of the Oligonucleotide Probes

1.1. Nucleic Acid Extraction.

A rapid extraction method based on physical disruption of the fungal cells followed by crude separation of the cell debris from the genomic DNA was used for the production of DNA from single colonies of yeasts (Roberts, 1997). For filamentous fungi, a more elaborate sample preparation method based on a combination of beadbeating and lysis with a GuSCN buffer followed by capturing of the DNA on silica was used.

1.2. PCR Amplification 20-50 ng genomic DNA or 5 µl of DNA extracted by the rapid extraction procedure described above were included in the PCR reaction. PCR reactions contained per 100 µl reaction: 200 µM of each dNTP's, 1×Taq buffer, 3 mM MgCl2, 15% glycerol, 40 pmol of each biotinylated primer (ITS5 and ITS4 for amplification of the full ITS region, ITS5 and ITS2 for amplification of ITS-1 only), 1 U Uracil N glycosylase and 2.5 U Taq polymerase. PCR thermal cycling conditions were the following: 95° C. for 10 min for 1 cycle (hotstart), 94° C. for 30 sec., 55° C. for 30 sec., 72° C. for 2 min. for 30 cycles, and a final extension at 72° C. for 10 min. for 1 cycle.

1.3. Production of LiPA Strips

Synthetic probes were provided enzymatically at the 3' end with a poly-T-tail using terminal deoxynucleotidyl transferase (Pharmacia) in a standard reaction buffer. After one hour incubation, the reaction was stopped and the tailed probes were precipitated and washed with ice-cold ethanol. The oligonucleotide probe sequences of the invention are indicated in Table 1.

If tailing occurred by chemical synthesis, the poly-T-tail was attached at the 5' end of the oligonucleotide probe. Chemically tailed probes may need a small modification (deletion and/or addition of a few nucleotides at one or both of the extremities) of the probe sequence as compared to the enzymatically tailed probe, in order to show comparable hybridization characteristics. The chemically tailed modified probes are indicated with the extension "(SGS)" in Table 1 and, if the modification is an addition of nucleotides, it is indicated in bold.

Probes were dissolved in 6×SSC at their respective specific concentrations and applied as horizontal lines on membrane strips. Biotinylated DNA was applied alongside as positive control. The oligonucleotides were fixed to the membrane by baking at 80° C. for 12 hours. The membrane was than sliced into 4 mm strips.

1.4. LiPA Test Performance

Equal volumes (5 to 10 µl) of the biotinylated PCR fragments and of the denaturation solution (400 mM NaOH/10 mM EDTA) were mixed in test troughs and incubated at room temperature for 5 min. Subsequently, 2 ml of the 50° C. prewarmed hybridization solution (2×SSC/0.1% SDS) was added followed by the addition of one strip per test trough. Hybridization occurred for 1 hour at 50° C. in a closed shaking water bath. The strips were washed twice with 2 ml of stringent was solution (2×SSC, 0.1% SDS) at room temperature for 20 sec., and once at 50° C. for 15 min. Following this stringent wash, strips were rinsed two times with 2 ml of the Innogenetics standard Rinse Solution (RS). Strips were incubated on a rotating platform with the alkaline phosphatase-labelled streptavidin conjugate, diluted in standard Conjugate Solution (CS) for 3 min. at room temperature. Strips were then washed twice with 2 ml of RS and once with standard Substrate Buffer (SB), and the colour reaction was started by adding BCIP and NBT to the SB. After 30 min. at room temperature, the colour reaction was stopped by replacing the colour compounds by distilled water. Immediately after drying, the strips were interpreted. The complete procedure described above can also be replaced by the standard Inno-LiPA automation device (Auto-LiPA. Innogenetics N.V., Zwijnaarde, Belgium). The above mentioned buffers (RS, CS, SB) may all be obtained from Innogenetics N.V. (Zwijnaarde, Belgium).

1.5. Hybridization Results

Specific hybridization results for a set of probes of Table 1 are summarized in Table 2. Species-specificity occurs when all the strains belonging to the respective fungal species show positive hybridization (−) and none of the other fungal species tested shows cross reaction with the species-specific probes under the hybridization conditions used.

FIG. 1 represents an example of LiPA strips. By comparing lanes 3, 9, 11, 15 and 17 with respectively lanes 2, 8, 10, 14 and 16 it is clear that the sensitivity of detection is higher (i.e. stronger hybridization signal obtained) when only the ITS-1 region is amplified, as compared to amplification of the full ITS region.

2. Sensitivity Testing of the PCR Amplification 2.1. Nucleic Acid Extraction

Small modifications were made on large-scale DNA extraction methods as described in literature (Holmes et al. 1994, Nho et al. 1997, Weig et al. 1997) and used to extract genomic DNA from *Candida, Cryptococcus* and *Aspergillus* species yielding DNA of high purity suitable for long term storage. DNA concentrations of the prepared stocks were calculated based on optical density measurements.

2.2. Sensitivity Testing

Amplification experiments were performed on dilution series of genomic DNA (ranging from 50 or 100 ng to 50 or 100 fg) using different primersets, either combination of ITS5/ITS2 amplifying the ITS-1 region only or ITS5/ITS4 amplifying the fall ITS region. Amplicons generated were visualised on ethidium-bromide stained gels and hybridized to LiPA strips containing the appropriate probes.

2.3. Results

Table 3 below summarizes the detection limits obtained with dilution series of genomic DNA isolated from the following organisms: *C. albicans, C. neoformans* and *A. fumigatus*.

| Organism | Amplification | Agarosegel | LiPA Hybridization |
|---|---|---|---|
| C. albicans | ITS1 | 10 pg | 100 fg |
|  | Full ITS | 1 pg | 100 fg |
| C. neoformans | ITS1 | 100 pg | 1 pg |
|  | Full ITS | 10 pg | 10 pg |
| A. fumigatus | ITS1 | 500 fg | 50 fg |
|  | Full ITS | 5 pg | 5 pg |

Amplification of the full ITS region results in a better sensitivity when amplicons are visualized on ethidiumbromide stained agarose gels (except for *A. fumigatus*). Inadequate staining of small amplicons could explain this phenomenon.

When hybridized to probes immobilized on LiPA strips (see e.g. FIG. 1), it is clearly seen that amplification of the ITS-1 region (smaller amplicon) results in a more sensitive detection limit compared to full ITS amplification. LiPA was able to specifically detect *C. albicans* DNA down to 100 fg, *Cryptococcus neoformans* DNA down to 1 pg, and *A. fumigatus* DNA down to 50 fg.

3. Sensitivity Testing in Spiked Sputum Samples 3.1. Nucleic Acid Extraction

200 μl sputum specimens were spiked with dilutions of *C. albicans* cells ($10^5$-1 cells/ml) or decreasing amounts (not quantifiable) of *A. fumigatus* mycelia. Fungal DNA was isolated from these sputum specimens using a modification of the method described by Boom et al., 1990. The overall time taken to process 15 sputum specimens was 2 hours.

3.2. Amplification

5 μl of the extracted DNA was used as target material in the PCR (100 μl). PCR reactions were carried out as described above. ITS-1 amplification was performed using primer combination ITS5+ITS2 and amplification of the full ITS region was performed using ITS5 and ITS4 primers.

3.3. Results

Following LiPA hybridization of the obtained amplicons a detection limit of 10-100 cells/ml sputum was obtained for *C. albicans*. Amplification of spiked sputum specimens with *A. fumigatus* mycelia resulted in a detection of the lowest level of spiked *A. fumigatus* mycelium.

4. Sensitivity Testing in Spiked Blood Samples

Evaluation of different methods for the extraction of fungal DNA from blood has previously been reported in the literature (Loffler et al. 1997). Most of the methods evaluated involved known enzymatic approaches with some modifications. However, these methods failed to consistently yield high quality DNA resulting in variation in the detection limits achieved between experiments (data not shown). It was also noted that DNA extracted from *A. fumigatus* using these methods required a "hot start" PCR approach for sensitive PCR amplification of the extracted DNA (data not shown). As a result, a new sample pretreatment method for blood samples was developed by the current invention, as described below.

4.1. Nucleic Acid Extraction

200 μl, 1 ml and 5 ml blood samples were inoculated with decreasing concentrations of *C. albicans* cells ($10^5$-$10^1$ cells). The inoculated blood samples were pre-treated to lyse and remove the red blood cells. Blood samples of 200 μl were lysed in 800 μl of lysis buffer (10 mM Tris-HCl, [pH 7.5], 10 mM EDTA, 50 mM NaCl) at room temperature for 10 minutes and centrifuged at 13,000 rpm for 5 min, the supernatant discarded and the pellet was resuspended in 100 μl of sterile $H_2O$. Blood samples of 1 ml and 5 were lysed in 3 mls of lysis buffer and centrifuged at 2000 rpm for 10 mins, the supernatant discarded and the pellet was resuspended in 100 μl of sterile $H_2O$. Glass beads (0.5 mm zirconium glass beads stored in 0.2% SDS) were added to the resuspended pellet, the sample was vortexed in a mini-bead beater at top speed for 190 seconds in order to mechanically disrupt the yeast cells. The DNA was subsequently extracted using known methods such as e.g. described by Boom et al. (1999) or the QIAmp Tissue kit (Qiagen, Los Angeles, Calif.).

This same method proved to be applicable also to other fungal species, such as *Aspergillus* and *Cryptococcus* spp.

4.2. Amplification

PCR amplification of the ITS region was performed in a final volume of 100 µl with 20 µl of DNA extracted from the blood samples (for DNA extracted from 5 ml blood samples, 20 µl of a 1/10 dilution is included in the POR reaction) added to the PCR reaction containing a final concentration 0.25 mM deoxynucleotidetriphosphates (DU/dNTP's [2:1]), 1× reaction buffer (Promega, USA), 3 mM $MgCl_2$, 1 unit Uracil DNA glycosylase (Longo et al 1990; Roche-Boehringer Mannheim, Germany), 40 pmol each of the forward ITS5 primer (5'-GAAAGTAAAAGTCGTAACAAGG-3') (SEQ ID NO:50) and reverse primer ITS4 (5'-TCCTCCGCTTAT-TGATATGC-3') (SEQ ID NO:45), 2.5 units of Taq polymerase (Promega, USA), made to a final volume of 100 µl in nuclease free water (Sigma-Aldrich Ltd, UK).

PCR amplification was performed in a Touchdown™ Thermocycler (Hybaid, UK), with the following cycling conditions: 37° C. for 10 minutes for 1 cycle followed by 94° C. for 2 minutes for 1 cycle followed by 40 cycles of DNA denaturation at 94° C. for 30 seconds, primer annealing at 55° C. for 30 seconds and DNA extension at 72° C. for 2 minutes, with a final extension cycle at 72° C. for 10 minutes. 50 ng of *C. albicans* DNA extracted as described above was included as a positive control in the PCR reaction along with a no template negative control in each PCR run.

4.3. LiPA Hybridization Results and Evaluation of the Test Performance.

Following LiPA hybridization of the obtained amplicons, a detection limit of 2-10 cells/ml blood was consistently obtained for *Candida albicans* (results not shown). The PCR-LiPA and associated extraction of fungal DNA from blood samples can be performed in a single working day while the technology itself may be easily integrated into a clinical testing laboratory that is already engaged in PCR as it does not require any specialised equipment.

Early reports of PCR-based assays for the detection of *Candida* in blood describe hemi-nested approaches (Rand et al. 1994) or rely on cumbersome laboratory-based techniques for post-PCR detection (Holmes et al., 1994; Jordan et al. 1994) which are unsuitable for large scale screening of samples. More recent reports describe a number of different approaches for the detection of fungal pathogens in blood. These include a broad spectrum PCR-based approach (Van Burik et al., 1998) designed to detect the presence of fungal infection in blood without identification of the specific infectious agent but with a detection sensitivity of 4 cells/ml following hybridisation with a non-radioactive pan-fungal DNA probe. The authors describe the successful application of this assay to the detection of fungal infection in samples from a group of bone marrow transplant patients. A microtitre-plate based assay for the detection of the five most clinically significant *Candida* species has also been described (Shin-Ichi et al. 1995) and while they report a detection sensitivity of 2 cells/200 µl of blood, the assay technology may be a little cumbersome as the post-PCR hybridisation of the amplicons to the species-specific probes is performed in microcentrifuge tubes and then transferred to a microtitre-plate for the detection step. A more recent publication (Hee Shin et al. 1999) describes a very elegant assay for the detection of up to three *Candida* species in a single reaction tube by using DNA probes labelled with different fluorescent tags. This assay represents a two-step system, with the PCR amplification and post-PCR detection being performed in a single tube and reducing the assay time from 7 hours to 5 hours. The authors describe the application of the assay technology for the detection of *Candida* in blood culture bottles positive for the presence of fungal infection.

The PCR-LiPA assay described in the current invention is also a multi-parameter test as a single LiPA membrane includes DNA probes for the detection of a wide range of different *Candida* species. It therefore has the potential to detect and identify mixed *Candida* infections. Moreover, a universal approach for the preparation of fungal DNA from *Candida. Cryptococcus* and *Aspergillus* ssp. in blood and/or respiratory specimens has been developed, as described above (see 4.1).

5. Testing of Clinical Isolates

Fungal DNA extraction was performed on cultures of clinical isolates using the methods as described above. PCR reactions were carried out as described above and primer combination ITS5+ITS4 was used for full ITS amplification.

LiPA strips for fungal pathogens were evaluated on 100 clinical isolates. The full ITS region was amplified from 75 clinical isolates of dimorphic yeasts following the application of the rapid preparation method (Roberts et al. 1997) from a single colony. The full ITS region was amplified from 25 clinical isolates of filamentous fungi, following preparation of the DNA using the modified Boom et al. method.

Hybridization of the obtained PCR products to the LiPA strips identified 2 isolates as *C. parapsilosis*, 2 isolates as *C. glabrata*, 15 isolates as *A. fumigatus*, 3 isolates as *A. nidulans*, 3 isolates as *A. flavus* and 5 unidentified isolates (=belonging to other fungal species for which no probes were present on the LiPA strip, but for which an amplicon was obtained during the fungal-universal PCR reaction). All remaining isolates were identified as *C. albicans* and these were confirmed using a biochemical diagnostic kit "Murex *C. albicans*" (Murex Diagnostica). An example of the LiPA hybridization results obtained with 15 clinical isolates is shown on FIG. 2.

The above results convincingly show that the probes of the current invention are not only applicable for the detection of laboratory fungal strains, from which they were originally designed, but that they detect with high specificity and sensitivity clinically occurring strains of those fungal species. The methods described in the current invention will therefore greatly facilitate the detection of fungal pathogens in clinical samples, if desirable in one single assay.

REFERENCES

Asseline U, Delarue M, Lancelot G, Toulme F, Thuong N (1984) Nucleic acid-binding molecules with high affinity and base sequence specificity: intercalating agents covalently inked to oligodeoxynucleotides. Proc. Natl. Acad. Sci. USA 81(11): 3297-301.

Bart-Delabesse, E., P. Boiron, A. Carlotti, and B. Dupont. 1993. *Candida albicans* genotyping in studies with patients with AIDS developing resistance to fluoconazole. J. Clin. Microbiol. 31: 2933-2937.

Bej A, Mahbubani M, Miller R, Di Cesare. J, Haff L, Atlas R. Multiplex PCR amplification and immobilized capture probes for detection of bacterial pathogens and indicators in water. Mol Cell Probes 1990; 4: 353-365.

Boom et al. 1990. Rapid and simple method for purification of nucleic acids. J Clin Microbiol. 28(3): 495-503.

Boom et al. 1999. Improved silica-guanidiniumthiocyanate DNA isolation procedure based on selective binding of bovine alpha casein to silica particles. J. Clin. Microbiol. 37: 615-719.

Botelho A. and Planta R. 1994. Specific identification of *Candida albicans* by hybridization with oligonucleotides derived from ribosomal DNA internal spacers. Yeast, 10: 709-717.

Brawner, D. L. 1991. Comparison between methods of serortyping of *Candida albicans* produces discrepancies in results. J. Clin. Microbiol. 29: 1020-1025.

Bretage, S., J. M. Costa, A. Marmorat-Khuong, F. Poron, C. Cordonnier, M. Vidaud, and J. Fleury-Feith. 1995. Detection of *Aspergillus* species DNA in bronchoalveolar lavage samples by competitive PCR. J. Clin. Microbiol. 33: 1164-1168.

Chuck, S. L., and M. A. Sande. 1989. Infections with *Cryptococcus neoformans* in the acquired immunodeficiency syndrome. N. Engl. J. Med. 321: 794-799.

Cregan, P., A. Yamamoto. A. Lum, T. van der Heide, M. MacDonald, and L. Pulliam. 1990. Comparison of four methods for rapid detection of *Pneumocystis carinii* in respiratory specimens. J. Clin. Microbiol. 28: 2432-2436.

Duck P. Probe amplifier system based on chimeric cycling oligonucleotides. Biotechniques 1990; 9: 142-147.

Einsele et al. 1997. Detection and identification of fungal pathogens in blood by using molecular probes. J. Clin. Microbiol. 35(6): 1353-1360.

Elie, C., Lott, T., Reiss, E. and Morrison C. 1998. Rapid identification of *Candida* species with species specific DNA probes. J. Clin. Microbiol. 36(11): 3260-3265.

Fisher, B. D., D. Armstrong, B. Yu, and J. W. M. Gold. 1981. Invasive aspergillosis: progress in early diagnosis and treatment. Am. J. Med. 71: 571-577.

Fletcher et al. 1998. Detection of *Aspergillus fumigatus* PCR products by a microtitre plate based DNA hybridisation assay. J Clin Pathol. 51(8): 617-20.

Fujita, S., Lasker B., Lott, T., Reiss, E. and Morrison C. 1995. Microtitration Plate Enzyme Immunoassay to detect PCR amplified DNA from *Candida* species in blood. J. Clin. Microbiol. 33(4): 962-967.

Goodwin, S. D., J. Fiedler-Kelly, T. H. Grasela, W. A. Schell, and J. R. Perfect. 1992. A nationwide survey of clinical laboratory methodologies for fungal infections. J. Med. Vet. Mycol. 30: 153-160.

Guatelli J, Whitfield K, Kwoh D, Barringer K, Richman D, Gengeras T. Isothermal, in vitro amplification of nucleic acids by a multienzyme reaction modeled after retroviral replication. Proc Natl Acad Sci USA 1990; 87: 1874-1878.

Hee Shin et al. 1999. Rapid identification of up to three *Candida* species in a single reaction tube by a 5' exonuclease asssay using fluorescent DNA probes. J. Clin. Microbiol. 37: 165-170.

Heimdahl, A., and C. K. Nord. 1990. Oral yeast infections in immunocompromised and seriously diseased patients. Acta Odontol. Scand. 48: 77-84.

Holmes, A. R. et al. 1994. Detection of *Candida albicans* and other yeasts in blood by PCR. J. Clin. Microbiol. 32(1): 228-231.

Jordan, J. A. 1994. PCR identification of four medically important *Candida* species by using a single primer pair. J. Clin. Microbiol. 32: 2962-2967.

Kohno, S., A. Yasuoka, H. Koga, M. Kaku, S. Maesaki, K. Tanaka, K. Mitsutake, H. Matsuda, and K. Hara. 1993. High detection rates of cryptococcal antigen in pulmonary cryptococcosis by Eiken latex agglutination test with pronase pretreatment Mycopathologia 123: 75-79.

Kumeda, Y., and T. Asao. 1996. Single-strand conformation polymorphism analysis of PCR-amplified ribosomal DNA internal transcribed spacers to differentiate species of *Aspergillus* section Flavi. Appl. Environm. Microbiol. 62: 2947-2952.

Kwoh D, Davis G, Whitfield K, Chappelle H, Dimichele L, Gingeras T. Transcription-based amplification system and detection of amplified human immunodeficiency virus type 1 with a bead-based sandwich hybridization format. Proc Natl Acad Sci USA 1989; 86: 1173-1177.

Landgren U, Kaiser R, Sanders J, Hood L. A ligase-mediated gene detection technique. Science 1988; 241: 1077-1080.

Loffler et al. 1997. Comparison of different methods for extraction of fungal pathogens from cultures and blood. J. Clin. Microbiol. 35: 3311-3312.

Longo et al. 1990. Use of Uracil DNA glycosylase to control carry over contamination in PCR. Gene 93: 125-128.

Lomeli H, Tyagi S, Printchard C, Lisardi P, Kramer F. Quantitative assays based on the use of replicatable hybridization probes. Clin Chem 1989; 35: 1826-1831.

Lu, J., C. Chi-Hsiang, M. S. Bartlett. J. W. Smith, and C. Lee. 1995. Comparison of six different PCR methods for detection of *Pneumocystis carinii*. J. Clin. Microbiol. 33: 2785-2788.

Lu, J., C. Bartlett, J. W. Smith, and C. Lee. 1997. Typing of *Pneumocystis carinii* strains with type specific oligonucleotide probes derived from the nucleotide sequences of Internal Transcribed Spacers of rRNA genes. J. Clin. Microbiol. 33: 2973-2977.

Miller P, Yano J, Yano E, Carroll C, Jayaram K, Ts'o P, 1979. Nonionic nucleic acid analogues. Synthesis and characterization of dideoxyribonucleoside methylphosphonates. Biochemistry 18(23): 5134-43.

Nho, S. et al. 1997. Species differentiation by internally transcribed spacer PCR and HhaI digestion of flucanozole-resistant *Candida krusei, Candida inconspicua*, and *Candida norvegensis* strains. J. Clin. Microbiol. 35 (4): 1036-1039.

Nielsen P, Egholm M, Berg R, Buchardt O (1991) Sequence-selective recognition of DNA by strand displacement with a thymine-substituted polyamide. Science 254(5037): 1497-500.

Rand et al. 1994. Detection of candidemia by PCR. Mol. Cell. probes 8: 215-222.

Rinaldi, M. G. 1988. *Aspergillus*, p. 559-572. In A. Balows, W. J. Hausler, Jr., M. Ohashi, and A. Turano (ed.), *Laboratory Diagnosis of Infectious Diseases. Principles and Practice*, vol. 1. *Bacterial, Mycotic and Parasitic Diseases*. Springer-Verlag, New York.

Roberts, D. M. 1997. Genome analysis of plant and insect pathogenic species of *Verticillium* using molecular methodologies. Ph.D. thesis, University of London.

Rogers, T. R., K. A. Haynes, and R. Barnes. 1990. Value of antigen detection in predicting invasive aspergillosis. Lancet 336: 1210-1213.

Sabetta, J. R., P. Miniter, and V. T. Andriole. 1985. The diagnosis of invasive aspergillosis by enzyme-linked immunosorbent assay for circulating antigen. J. Infect. Dis. 152: 946-953.

Saiki R, Walsh P, Levenson C, Erlich H. 1988. Genetic analysis of amplified DNA with immobilized sequence-specific oligonucleotide probes Proc Natl Acad Sci USA 86: 6230-6234.

Shin J. H., Nolte, F., Holloway, B. and Morrison C. 1999. Rapid identification of up to three *Candida* species in a single reaction tube by a 5' exonuclease assay using fluorescent DNA probes. J. Clin. Microbiol. 37(1): 165-170.

Shin-Ichi, et al. 1995. Microtitration plate enzyme immunoassay to detect PCR amplified DNA from *Candida* species in blood. J. Clin. Microbiol. 33: 962-967.

Sobczak, H. 1985. A simple disc-diffusion test for differentation of yeast species. J. Med. Microbiol. 20: 307-316.

Soll, D. R. 1992. High-frequency switching in *Candida albicans*. Clin. Microbiol. Rev. 5: 183-203.

Stringer, J. R. 1996. *Pneumocystis carinii*: What is it, exactly? Clin. Microbiol. Rev. 9: 489-498.

Stuyver, L. et al. 1993. Typing of hepatitis C virus isolates and characterization of new subtypes using a line probe assay. J. Gen. Virology, 74: 1093-1102.

Van Burik, et al. 1998. Panfungal PCR assay for detection of fungal infection in human blood specimens. J. Clin. Microbiol. 36: 1169-1175.

Weig, M. et al. 1997. Usefulness of PCR for diagnosis of *Pneumocystis carinii* pneumonia in different patient groups. J. Clin. Microbiol. 35(6): 1445-1449.

White et al. 1990. Amplification and direct sequencing of fungal ribosomal RNA genes for phylogenetics. p. 315-322. In Innis et al. (ed.), PCR protocols. Academic Press, San Diego, Calif.

Williams, D. W., M. J. Wilson, M. A. O. Lewis, and A. J. C. Potts. 1995. Identification of *Candida* species by PCR and restriction fragment length polymorphism analysis of intergenic spacer regions of ribosomal DNA. J. Clin. Microbiol. 33: 2476-2479.

Williamson, M. I., L. P. Samaranayake, and T. W. MacFarlane. 1986. Biotypes of oral *Candida albicans* and *Candida tropicalis*. J. Med. Vet. Mycol. 24: 81-84.

The invention claimed is:

1. An isolated oligonucleotide molecule consisting of SEQ ID NO: 26, 41, or the RNA equivalents of said SEQ IDs wherein T is replaced by U, or the complements thereof.

2. A method to detect and identify at least one Aspergillus species in one single assay, including
   (i) releasing, isolating and I or concentrating the nucleic acids of the fungal pathogens possibly present in the sample,
   (ii) optionally, amplifying the Internal Transcribed Spacer region (ITS) of said nucleic acids with at least one fungal universal primer pair,
   (iii) hybridising the nucleic acids of step (i) or (ii) with at least one oligonucleotide molecule of claim 1,
   (iv) detecting the hybridisation complexes formed in step (iii), and
   (v) identifying the Aspergillus species present in said sample, based on the hybridisation complex formed.

3. Method according to claim 2, wherein said fungal universal primer pair is chosen from the following group of primer pairs:

```
ITS5:
GGAAGTAAAAGTCGTAACAAGG          (SEQ ID NO: 44)
and

ITS4:
TCCTCCGCTTATTGATATGC,           (SEQ ID NO: 45)

ITS5:
GGAAGTAAAAGTCGTAACAAGG          (SEQ ID NO: 44)
and

ITS2:
GCTGCGTTCTTCATCGATGC,           (SEQ ID NO: 46)
```

```
-continued
ITS1:
TCCGTAGGTGAACCTGCGG         (SEQ ID NO: 47)
and

ITS4:
TCCTCCGCTTATTGATATGC,       (SEQ ID NO: 45)

ITS1:
TCCGTAGGTGAACCTGCGG         (SEQ ID NO: 47)
and

ITS2:
GCTGCGTTCTTCATCGATGC,       (SEQ ID NO: 46)

ITS3:
GCATCGATGAAGAACGCAGC        (SEQ ID NO: 49)
and

ITS4:
TCCTCCGCTTATTGATATGC.       (SEQ ID NO: 45)
```

4. Method according to claim 2 wherein the *Aspergillus* species is *A. fumigatus* and wherein the at least one oligonucleotide molecule of step (iii) is chosen from among SEQ ID NOs:26 and 41.

5. Method according to claim 2 wherein the at least one oligonucleotide molecule of step (iii) is immobilized to a solid support.

6. Method according to claim 2, further enabling the detection and identification of at least one of the following fungal pathogens: *Candida albicans, Candida parapsilosis, Candida tropicalis, Candida kefyr, Candida krusei, Candida glabrata*, and/or *Candida dubliniensis*, wherein the nucleic acids of step (i) or (ii) are further hybridized with at least one of the following species specific oligonucleotide probes: SEQ ID NOs:2 to 13, and 33 to 38.

7. Method for the simultaneous detection and differentiation of at least two *Aspergillus* species in one single assay, including
  (i) releasing, isolating and I or concentrating the nucleic acids of the fungal pathogens possibly present in the sample,
  (ii) optionally, amplifying the Internal Transcribed Spacer region (ITS) of said nucleic acids with at least one fungal universal primer pair,
  (iii) hybridising the nucleic acids of step (i) or (ii) with at least two oligonucleotide molecules wherein at least one of the oligonucleotide molecules is an oligonucleotide of claim 1 and at least one of the oligonucleotides is selected from the group consisting of SEQ ID NOs: 18-27 and 40-43, under the same hybridization conditions,
  (iv) detecting the hybridisation complexes formed in step (iii), and
  identifying the *Aspergillus* species present in said sample, based on the hybridisation complex formed.

8. Method according to claim 7, wherein said fungal universal primer pair is chosen from the following group of primer pairs:

```
ITS5:
GGAAGTAAAAGTCGTAACAAGG      (SEQ ID NO: 44)
and

ITS4:
TCCTCCGCTTATTGATATGC,       (SEQ ID NO: 45)

ITS5:
GGAAGTAAAAGTCGTAACAAGG      (SEQ ID NO: 44)
and

ITS2:
GCTGCGTTCTTCATCGATGC,       (SEQ ID NO: 46)

ITS1:
TCCGTAGGTGAACCTGCGG         (SEQ ID NO: 47)
and

ITS4:
TCCTCCGCTTATTGATATGC,       (SEQ ID NO: 45)

ITS1:
TCCGTAGGTGAACCTGCGG         (SEQ ID NO: 47)
and

ITS2:
GCTGCGTTCTTCATCGATGC,       (SEQ ID NO: 48)

ITS3:
GCATCGATGAAGAACGCAGC        (SEQ ID NO: 49)
and

ITS4:
TCCTCCGCTTATTGATATGC.       (SEQ ID NO: 45)
```

9. A combination of at least two isolated oligonucleotide molecules consisting of at least one oligonucleotide molecule of claim 1 and a nucleotide sequence represented by any of SEQ ID NOs: 2 to 25, 27 to 40, 42 and 43, or the RNA equivalents of said SEQ IDs wherein T is replaced by U, or the complementary nucleic acid of said SEQ IDs, wherein said at least two oligonucleotide molecules are functional as hybridization probes under identical hybridization conditions.

* * * * *